(12) United States Patent
Dadd et al.

(10) Patent No.: US 8,909,349 B2
(45) Date of Patent: Dec. 9, 2014

(54) CARTRIDGE FOR AN ELECTRODE ARRAY INSERTION DEVICE

(75) Inventors: Fysh Dadd, Lane Cove (AU); Peter Gibson, South Coogee (AU); Miroslaw Mackiewicz, Ryde (AU); Katherine Meagher, Manly (AU); Claudiu Treaba, Centennial, CO (US); Henry Hon Sang Tsui, Mortdale (AU); Desmond McCusker, Balmain (AU)

(73) Assignee: Cochlear Limited, Macquarie University, NSW (AU)

( * ) Notice: Subject to any disclaimer, the term of this patent is extended or adjusted under 35 U.S.C. 154(b) by 65 days.

(21) Appl. No.: 12/875,847

(22) Filed: Sep. 3, 2010

(65) Prior Publication Data
US 2011/0218548 A1    Sep. 8, 2011

Related U.S. Application Data

(62) Division of application No. 10/505,075, filed as application No. PCT/AU03/00229 on Feb. 24, 2003, now Pat. No. 7,792,586.

(30) Foreign Application Priority Data

| Feb. 22, 2002 | (AU) | PS0720 |
| Feb. 22, 2002 | (AU) | PS0721 |
| Feb. 22, 2002 | (AU) | PS0722 |
| Feb. 22, 2002 | (AU) | PS0723 |
| Feb. 22, 2002 | (AU) | PS0724 |
| Apr. 22, 2002 | (AU) | PS1877 |
| Sep. 2, 2002 | (AU) | 2002951152 |

(51) Int. Cl.
*A61N 1/05* (2006.01)
*A61B 17/34* (2006.01)
*A61B 19/00* (2006.01)
*A61B 17/00* (2006.01)

(52) U.S. Cl.
CPC .......... *A61N 1/0541* (2013.01); *A61B 2019/304* (2013.01); *A61B 2017/00787* (2013.01); *A61B 2017/00477* (2013.01); *A61B 17/3468* (2013.01)
USPC .......................................................... 607/57

(58) Field of Classification Search
CPC ......................... A61N 1/0541; A61N 1/36032
USPC .............................................. 607/55–57, 137
See application file for complete search history.

(56) References Cited

U.S. PATENT DOCUMENTS

| 4,488,561 A | 12/1984 | Doring |
| 4,532,930 A | 8/1985 | Crosby et al. |

(Continued)

FOREIGN PATENT DOCUMENTS

| WO | WO 8900870 | 2/1989 |
| WO | WO 9324058 | 12/1993 |

(Continued)

OTHER PUBLICATIONS

Official Communication Issued in connection with European Patent Application No. 02704493, dated Aug. 13, 2008.

(Continued)

*Primary Examiner* — Eric D. Bertram
(74) *Attorney, Agent, or Firm* — K&L Gates LLP

(57) ABSTRACT

A device, system and method for inserting a pre-curved electrode array (100) held in a substantially straight configuration by a straightening member (101) into a cochlea of a subject. As the electrode array (100) is inserted into the cochlea by the device, the straightening member (101) is held by the device such that the electrode array (100) advances off the straightening member (101) such that it is free to take on its pre-curved configuration in the cochlea of the subject.

20 Claims, 26 Drawing Sheets

(56) References Cited

U.S. PATENT DOCUMENTS

| | | | |
|---|---|---|---|
| 4,898,183 | A | 2/1990 | Kuzma |
| 5,443,493 | A | 8/1995 | Byers et al. |
| 5,545,219 | A | 8/1996 | Kuzma |
| 5,558,673 | A | 9/1996 | Edwards et al. |
| 5,645,585 | A * | 7/1997 | Kuzma ............................ 623/10 |
| 5,810,852 | A | 9/1998 | Greenberg et al. |
| 5,999,859 | A | 12/1999 | Jolly |
| 6,070,105 | A | 5/2000 | Kuzma |
| 6,078,841 | A | 6/2000 | Kuzma |
| 6,119,044 | A | 9/2000 | Kuzma |
| 6,125,302 | A | 9/2000 | Kuzma |
| 6,149,657 | A * | 11/2000 | Kuzma ........................ 606/129 |
| 6,195,586 | B1 | 2/2001 | Kuzma |
| 6,208,882 | B1 | 3/2001 | Lenarz et al. |
| 6,421,569 | B1 | 7/2002 | Treaba et al. |
| 6,968,238 | B1 | 11/2005 | Kuzma |
| 7,063,708 | B2 | 6/2006 | Gibson et al. |
| 7,792,586 | B2 | 9/2010 | Dadd et al. |
| 2003/0171758 | A1* | 9/2003 | Gibson et al. ................ 606/129 |
| 2004/0127968 | A1 | 7/2004 | Kuzma et al. |
| 2004/0220651 | A1 | 11/2004 | Kuzma et al. |
| 2006/0058861 | A1 | 3/2006 | Gibson et al. |

FOREIGN PATENT DOCUMENTS

| | | |
|---|---|---|
| WO | WO 9840119 | 9/1998 |
| WO | WO 9911321 | 3/1999 |
| WO | WO 0064529 | 11/2000 |
| WO | WO 0071063 | 11/2000 |
| WO | WO 03070133 | 8/2003 |

OTHER PUBLICATIONS

Supplementary Partial European Search Report, EP 02 70 4493.2, May 15, 2006.

Official Communication issued in connection with European Patent Application No. 03742445, dated Dec. 7, 2009.

Supplementary Partial European Search Report issued in connection with European Patent Application No. 03742445, dated Mar. 7, 2006.

Office Action issued in connection with Canadian Patent Application No. 2,473,041, dated Sep. 29, 2009.

English Translation of Notification of Reasons for Refusal issued in connection with Japanese Patent Application No. 569,094/2003, dated Jul. 22, 2008.

International Preliminary Examination Report for PCT/AU2003/000229, dated May 24, 2004.

International Search Report for PCT/AU2003/000229, dated May 5, 2003.

Written Opinion for PCT/AU2003/00229, dated Jun. 30, 2003.

International Search report of PCT/AU02/00333, dated May 13, 2002.

International Preliminary Examination Report of PCT/AU02/00333, dated Sep. 20, 2002.

Schramm, "Surgical Technique for the Implantation of the Advance Bionics HiRes 90K Device with HiFocus Perimodiolar (Helix) Electrode", International Congress Series, vol. 1273, Nov. 2004, pp. 129-132 (Available online Oct. 30, 2004).

English Translation of Japanese Notice of Reasons for Rejection issued in connection with Japanese Patent Application No. 2007-312746, dated Nov. 9, 2010.

English Translation of Japanese Notice of Rejection issued in connection with Japanese Patent Application No. 2002-572924, dated Aug. 7, 2007.

Official Communication issued in connection with European Patent Application No. 02704493, dated Apr. 20, 2010.

Canadian Office Action issued in connection with Canadian Patent Application No. 2473041, dated Nov. 23, 2010.

* cited by examiner

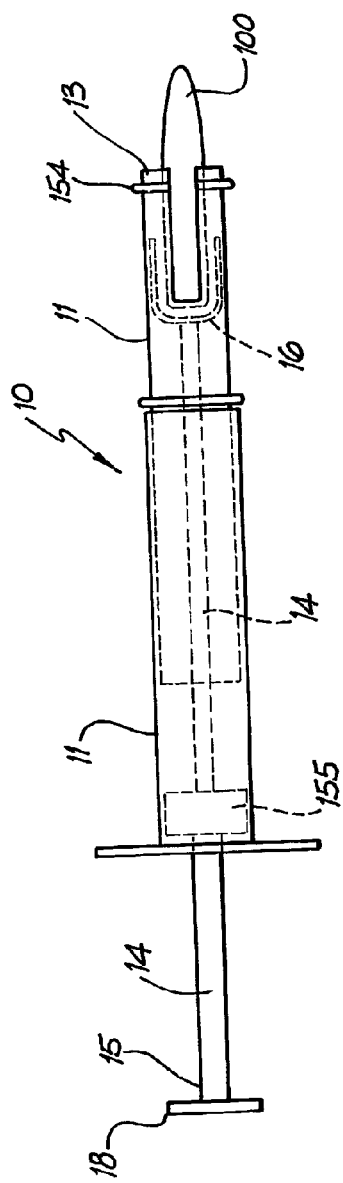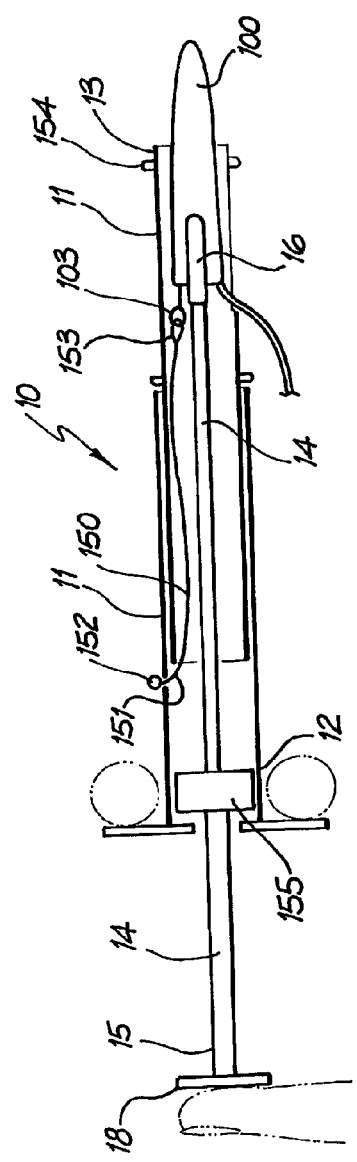
FIG. 11a
FIG. 11b

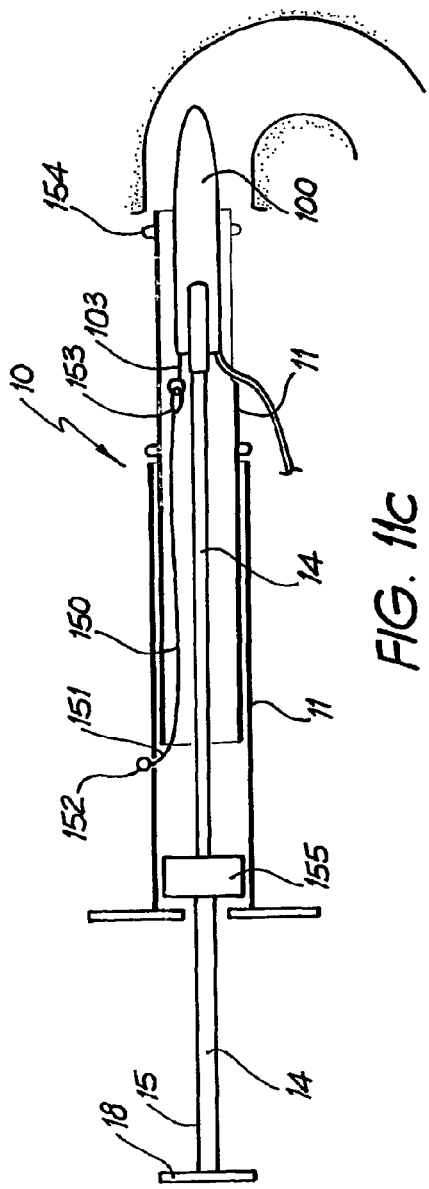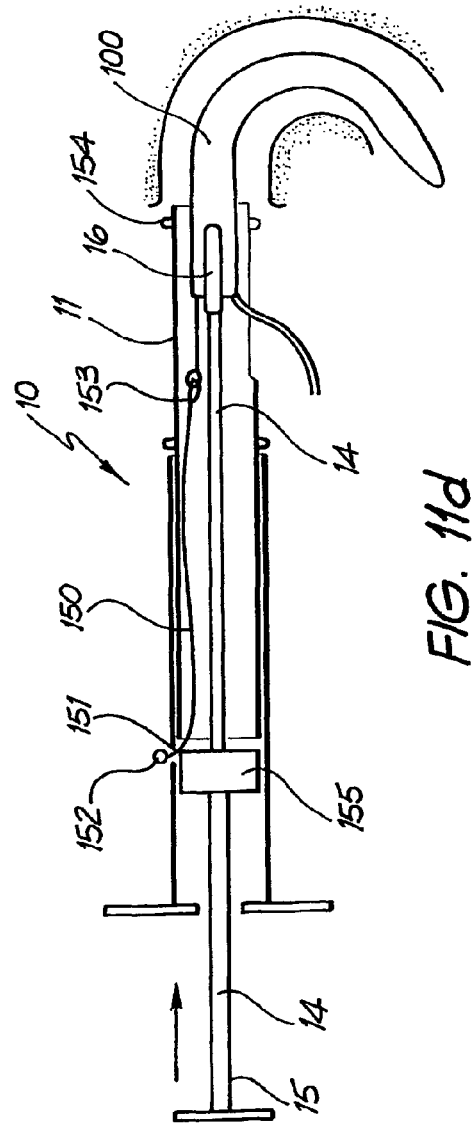

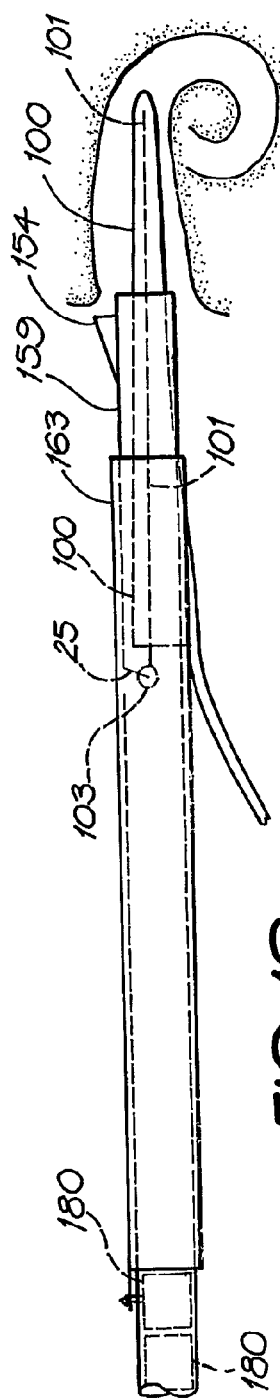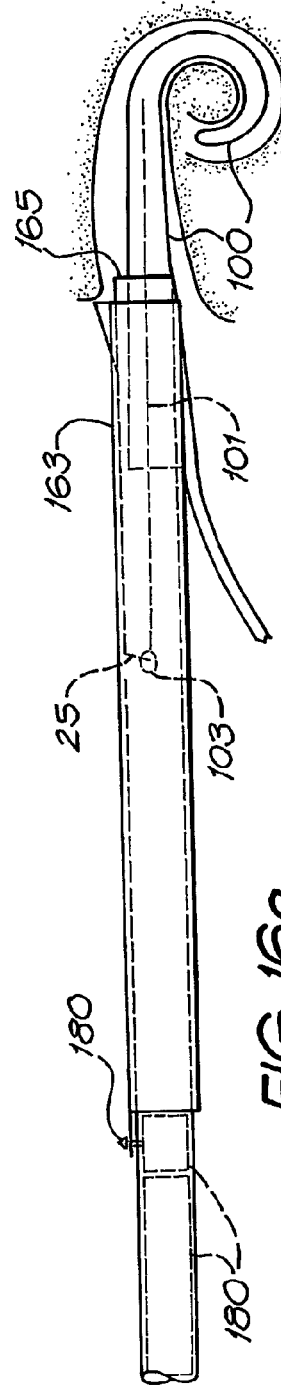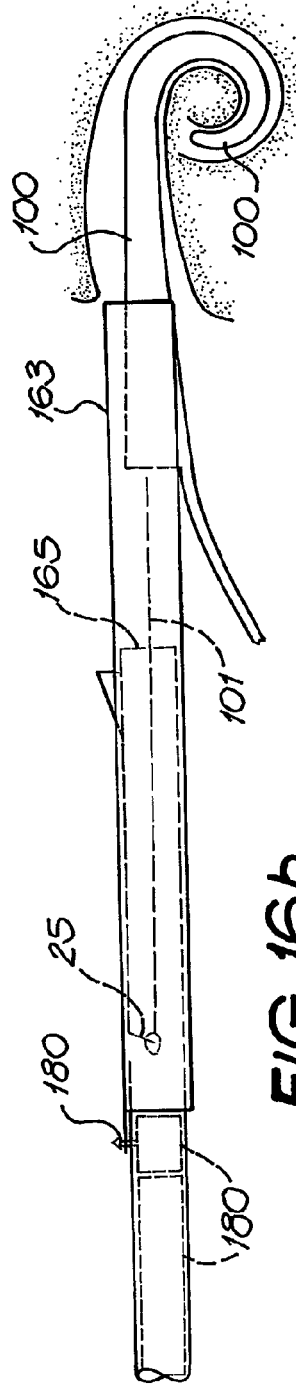

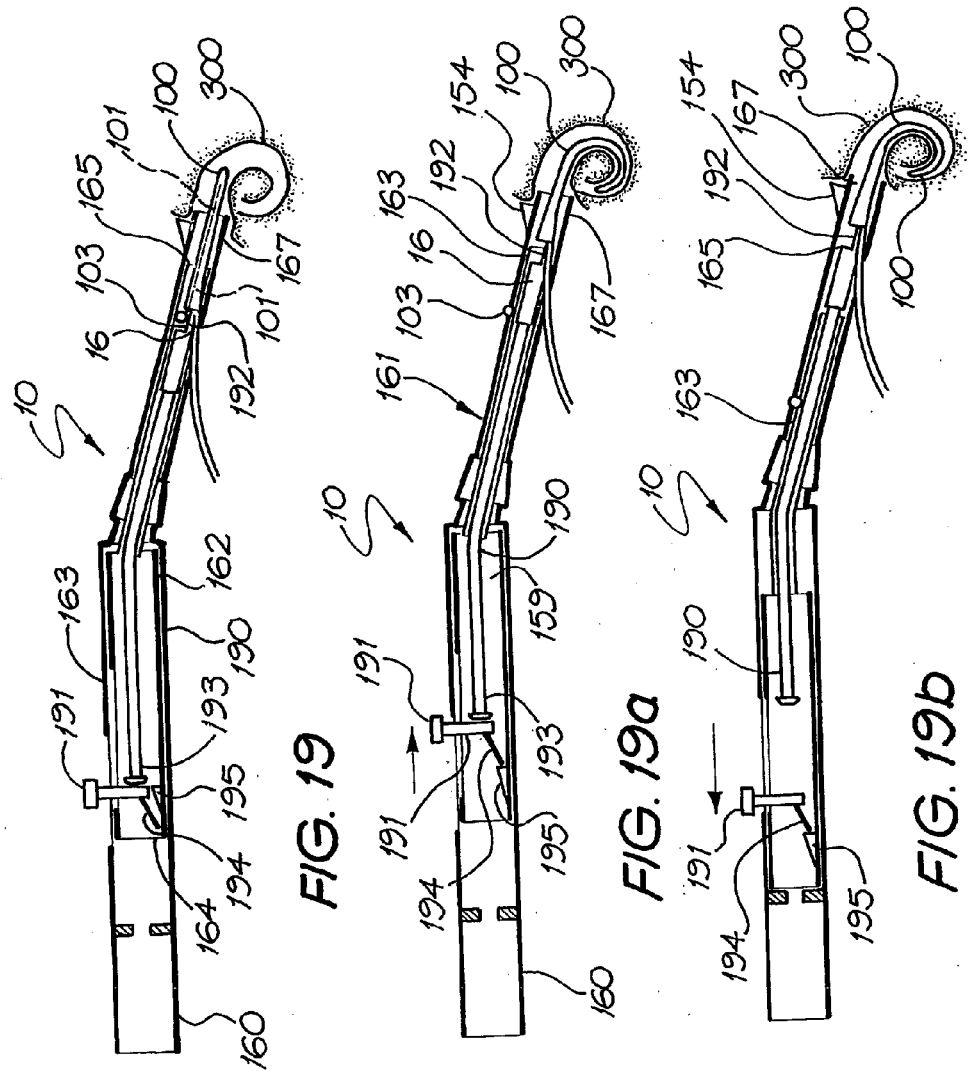

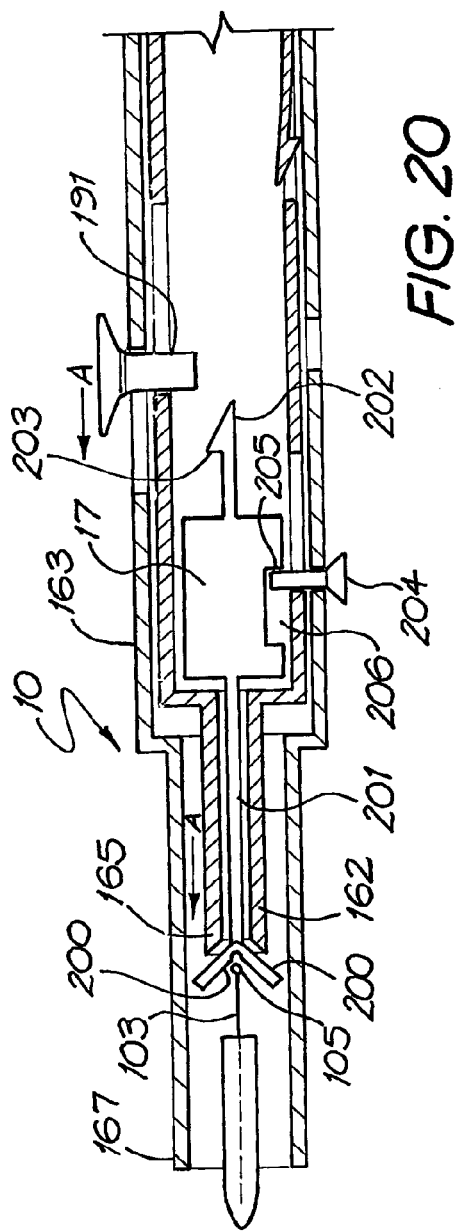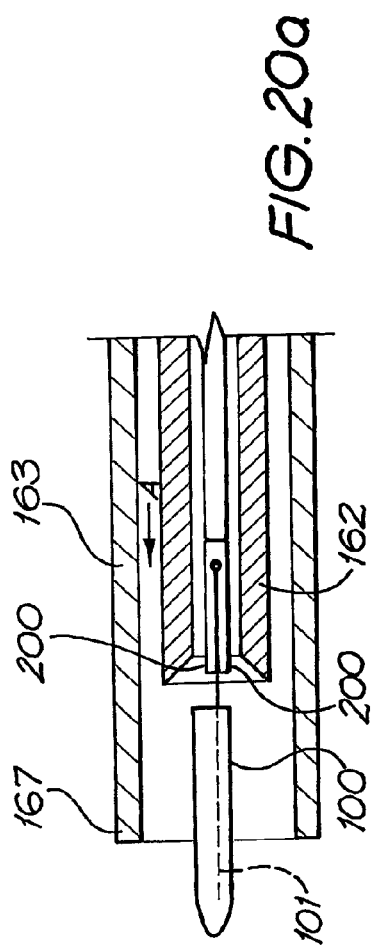

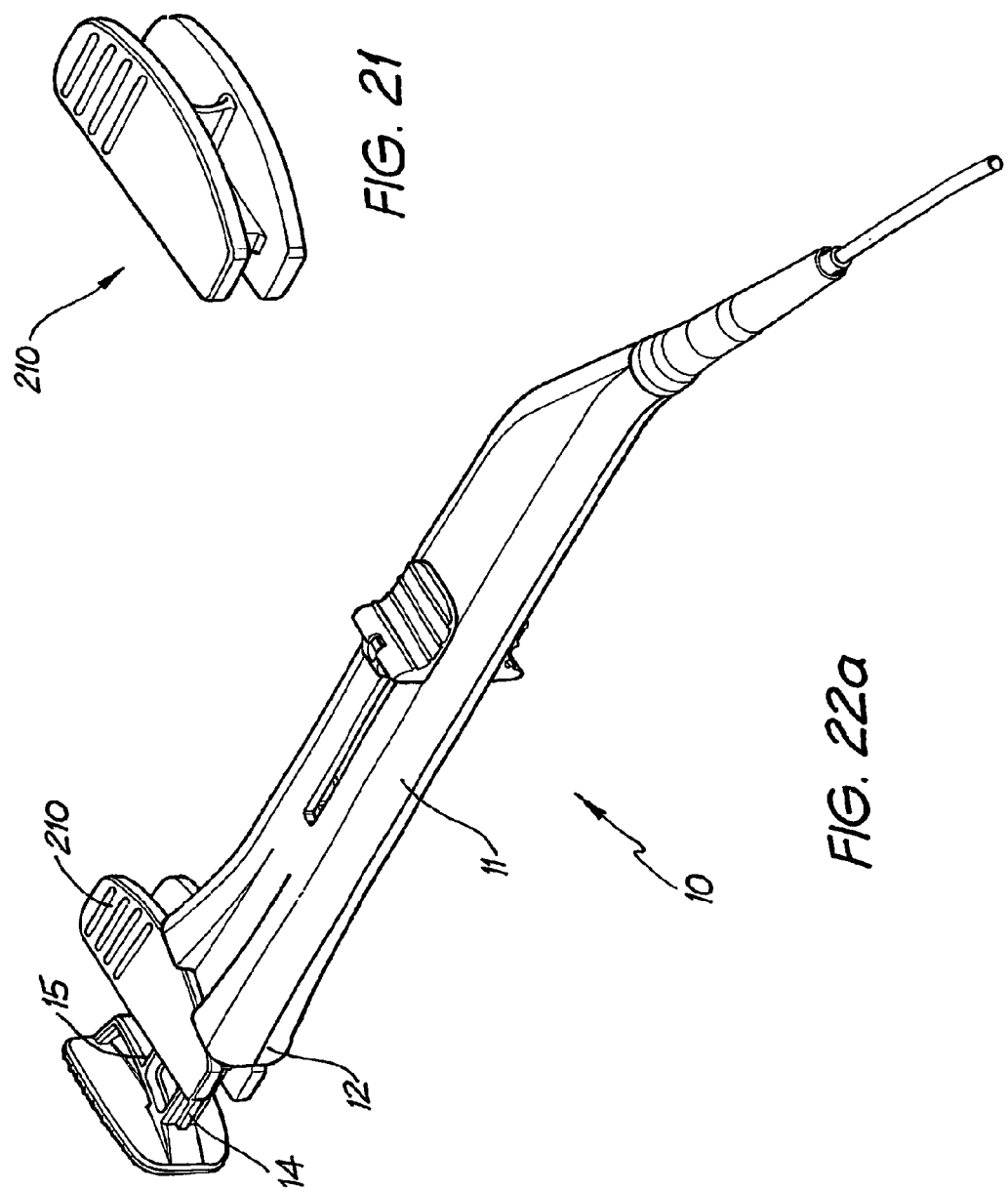

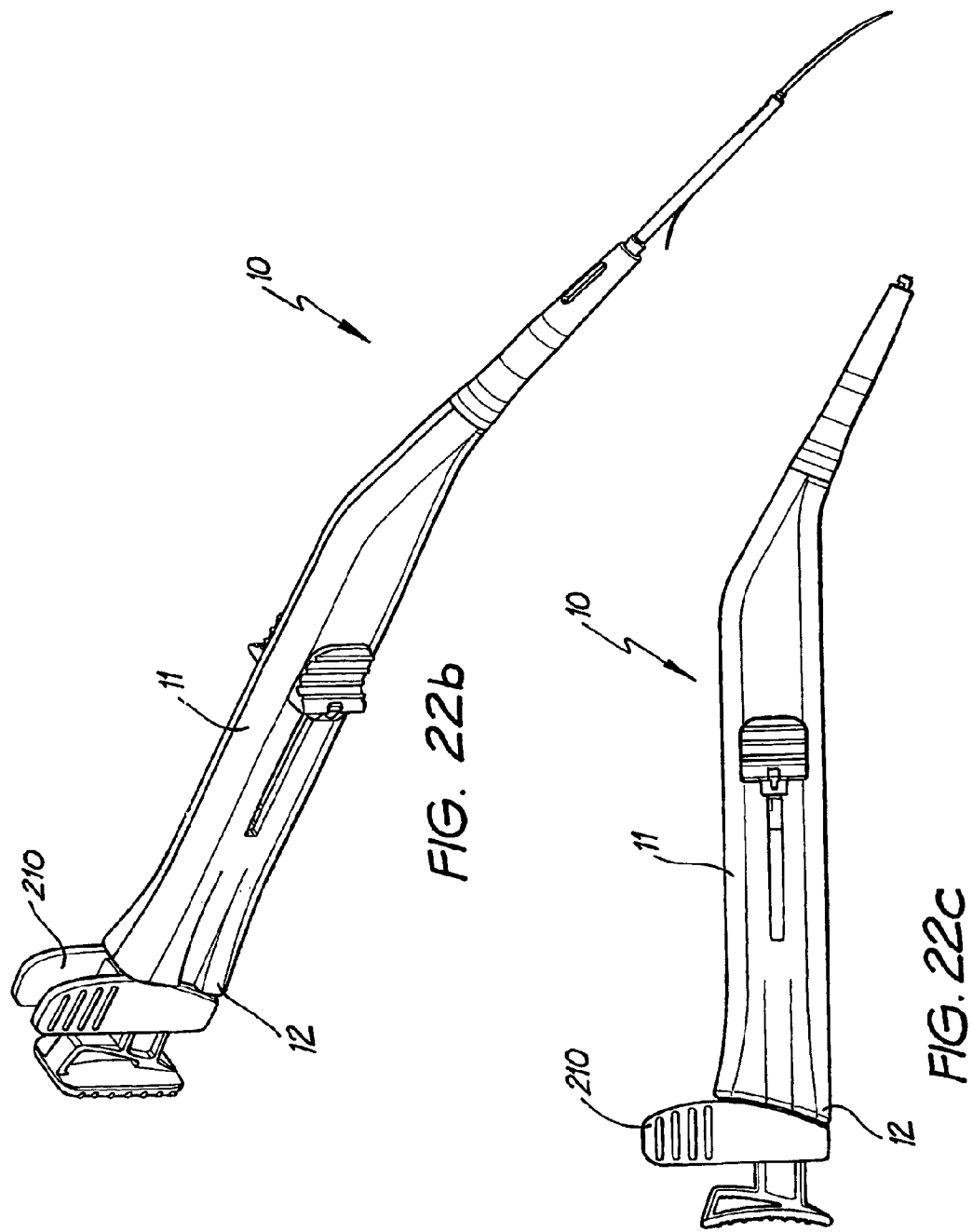

US 8,909,349 B2

CARTRIDGE FOR AN ELECTRODE ARRAY INSERTION DEVICE

CROSS-REFERENCE TO RELATED APPLICATION

This application is a Divisional of U.S. patent application Ser. No. 10/505,075, entitled "Insertion Device for an Electrode Array," filed on Mar. 10, 2006, which is now U.S. Pat. No. 7,792,586 which is a national stage application of PCT Application No. PCT/AU2003/000229, filed on Feb. 24, 2003, which claims priority from Australian Provisional Patent Application No. PS 0720, filed on Feb. 22, 2002, Australian Provisional Patent Application No. PS 0721, filed on Feb. 22, 2002, Australian Provisional Patent Application No. PS 0722, filed on Feb. 22, 2002, Australian Provisional Patent Application No. PS 0723, filed on Feb. 22, 2002, Australian Provisional Patent Application No. PS 0724, filed on Feb. 22, 2002, Australian Provisional Patent Application No. PS 1877, filed on Apr. 22, 2002, and Australian Provisional Patent Application No. 2002951152, filed on Sep. 2, 2002. Each of these documents is hereby incorporated by reference herein.

BACKGROUND

1. Field of the Invention

The present invention relates to a device, method and system for the insertion of an electrode array into a cochlea of a subject and the simultaneous removal of a straightening means of the electrode array.

2. Related Art

In many people who are profoundly deaf, the reason for deafness is absence or destruction of, the hair cells in the cochlea which transduce acoustic signals into nerve impulses. These people are unable to derive suitable benefit from conventional hearing aid systems, no matter how loud the acoustic stimulus is made, because there is damage to or absence of the mechanism for nerve impulses to be generated from sound in the normal manner.

It is for this purpose that cochlear implant systems have been developed. Such systems bypass the hair cells in the cochlea and directly deliver electrical stimulation to the auditory nerve fibers, thereby allowing the brain to perceive a hearing sensation resembling the natural hearing sensation normally delivered to the auditory nerve. U.S. Pat. No. 4,532,930 provides a description of one type of traditional cochlear implant system.

Typically, cochlear implant systems have consisted of essentially two components, an external component commonly referred to as a processor unit and an internal implanted component commonly referred to as a stimulator/receiver unit. Traditionally, both of these components have cooperated together to provide the sound sensation to a user.

The external component has traditionally consisted of a microphone for detecting sounds, such as speech and environmental sounds, a speech processor that converts the detected sounds, particularly speech, into a coded signal, a power source such as a battery, and an external transmitter coil.

The coded signal output by the speech processor is transmitted transcutaneously to the implanted stimulator/receiver unit situated within a recess of the temporal bone of the user. This transcutaneous transmission occurs via the external transmitter coil which is positioned to communicate with an implanted receiver coil provided with the stimulator/receiver unit.

This communication serves two essential purposes, firstly to transcutaneously transmit the coded sound signal and secondly to provide power to the implanted stimulator/receiver unit. Conventionally, this link has been in the form of a radio frequency (RF) link, but other such links have been proposed and implemented with varying degrees of success.

The implanted stimulator/receiver unit traditionally includes a receiver coil that receives the coded signal and power from the external processor component, and a stimulator that processes the coded signal and outputs a stimulation signal to an intracochlear electrode assembly which applies the electrical stimulation directly to the auditory nerve producing a hearing sensation corresponding to the original detected sound.

Traditionally, the external componentry has been carried on the body of the user, such as in a pocket of the users' clothing, a belt pouch or in a harness, while the microphone has been mounted on a clip behind the ear or on the lapel of the user.

More recently, due in the main to improvements in technology, the physical dimensions of the speech processor have been able to be reduced allowing for the external componentry to be housed in a small unit capable of being worn behind the ear of the user. This unit allows the microphone, power unit and the speech processor to be housed in a single unit capable of being discretely worn behind the ear, with the external transmitter coil still positioned on the side of the user's head to allow for the transmission of the coded sound signal from the speech processor and power to the implanted stimulator unit.

Together with improvements in available technology, much research has been undertaken in the area of understanding the way sound is naturally processed by the human auditory system. With such an increased understanding of how the cochlea naturally processes sounds of varying frequency and magnitude, there is a need to provide an improved cochlear implant system that delivers electrical stimulation to the auditory nerve in a way that takes into account the natural characteristics of the cochlea.

It is known in the art that the cochlea is tonotopically mapped. In other words, the cochlea can be partitioned into regions, with each region being responsive to signals in a particular frequency range. This property of the cochlea is exploited by providing the electrode assembly with an array of electrodes, each electrode being arranged and constructed to deliver a cochlea stimulating signal within a preselected frequency range to the appropriate cochlea region. The electrical currents and electric fields from each electrode stimulate the nerves disposed on the modiola of the cochlea.

It has been found that in order for these electrodes to be effective, the magnitude of the currents flowing from these electrodes and the intensity of the corresponding electric fields, are a function of the distance between the electrodes and the modiola. If this distance is relatively great, the threshold current magnitude must be larger than if the distance is relatively small. Moreover, the current from each electrode may flow in all directions, and the electrical fields corresponding to adjacent electrodes may overlap, thereby causing cross-electrode interference. In order to reduce the threshold stimulation amplitude and to eliminate cross-electrode interference, it is advisable to keep the distance between the electrode array and the modiola as small as possible. This is best accomplished by providing the electrode array in the shape which generally follows the shape of the modiola. Also, this way the delivery of the electrical stimulation to the auditory nerve is most effective as the electrode contacts are as close to the auditory nerves that are particularly responsive to selected pitches of sound waves.

In order to achieve this electrode array position close to the inside wall of the cochlea, the electrode needs to be designed in such a way that it assumes this position upon or immediately following insertion into the cochlea. This is a challenge as the array needs to be shaped such that it assumes a curved shape to conform with the natural shape of the inside wall of the cochlea and must also be shaped such that the insertion process causes minimal trauma to the sensitive structures of the cochlea. In this sense, it is desirable that the electrode array is held in a generally straight configuration at least during the initial stages of the insertion procedure.

Several procedures have been adopted to provide for an electrode assembly that is relatively straightforward to insert while adopting a curved configuration following insertion in the cochlea. In this regard, it is known to make an electrode array that includes a spiral-shaped carrier which has a natural spiral shape generally conforming to the configuration of a cochlea. Such an array may also include a straightening element or stylet to enable the carrier to be maintained in a straight configuration for insertion. The straightening member is then typically removed from the carrier following insertion thereby allowing the carrier to take on its natural spiral-shape and assume a position adjacent the inner wall of the cochlea. Such a configuration is described in the Applicant's issued U.S. Pat. No. 6,421,569.

Typically, the straightening member is removed following the insertion of the electrode array into the cochlea by clamping an exposed end of the straightening member with tweezers and gradually removing the stylet. This technique is difficult to coordinate and requires both hands of a surgeon to perform.

One problem with such a technique is that it is difficult to control the insertion process so that damage to the sensitive structures of the cochlea can be avoided. This is due to the fact that the cochlea has a natural spiral shape and the insertion of a substantially straight electrode array into such a space will cause the array to impact upon the walls of the cochlea, increasing the risk for damage to the cochlea walls if due care is not taken. It is typically not until the electrode array is fully inserted that the transition of the array from substantially straight to spirally curved is affected, hence the change transition does not aid in the insertion process as such.

A number of tools have been developed to assist in the insertion of the electrode array and subsequent removal of the straightening element. Typically, such devices have been difficult to use and have required complex sliding mechanisms to achieve the desired result. This has resulted in tools that are difficult to manufacture, difficult to clean for re-use, have an increased probability of failure due to their complexity, and which have not been specifically designed to control the shape transition of the electrode array to aid in a non-traumatic insertion procedure.

SUMMARY

In one aspect of the present invention, a cartridge configured to be received by an electrode array insertion device is disclosed. The cartridge comprises an elongate body extending from a first end to a second end and having a lumen extending therethrough, wherein the elongate body is configured to receive an electrode array in the lumen. The cartridge further comprises a window in a sidewall of the elongate body configured to allow viewing of a portion of the electrode array when the electrode array is positioned in the elongate body.

In another aspect of the present invention, a kit is disclosed. The kit comprises a straightening member, a pre-curved electrode array configured to be maintained in a substantially straight configuration when the straightening member is positioned along a substantial length of the electrode array, and a cartridge. The cartridge comprises an elongate body extending from a first end to a second end and having a lumen extending therethrough, wherein the elongate body is configured to receive the electrode array in the lumen; and a window in a sidewall of the elongate body configured to allow viewing of a portion of the electrode array when the electrode array is positioned in the elongate body.

In yet another aspect of the present invention, a system for inserting an electrode array into a cochlea of a subject is disclosed. The system comprises a straightening member, a pre-curved electrode array configured to be maintained in a substantially straight configuration when the straightening member is positioned along a substantial length of the electrode array, a cartridge configured to receive the electrode array; and an insertion device configured to receive at least a portion of the cartridge when the electrode array is positioned therein. The insertion device is configured to effect movement of the electrode array from a first position to a second position relative to the insertion device and to substantially prevent the straightening member from moving with the electrode array from the electrode array's first position to the electrode array's second position.

BRIEF DESCRIPTION OF THE DRAWINGS

FIGS. 11a to 22c depict further embodiments of the device of the present invention.

DETAILED DESCRIPTION

Figure 1:
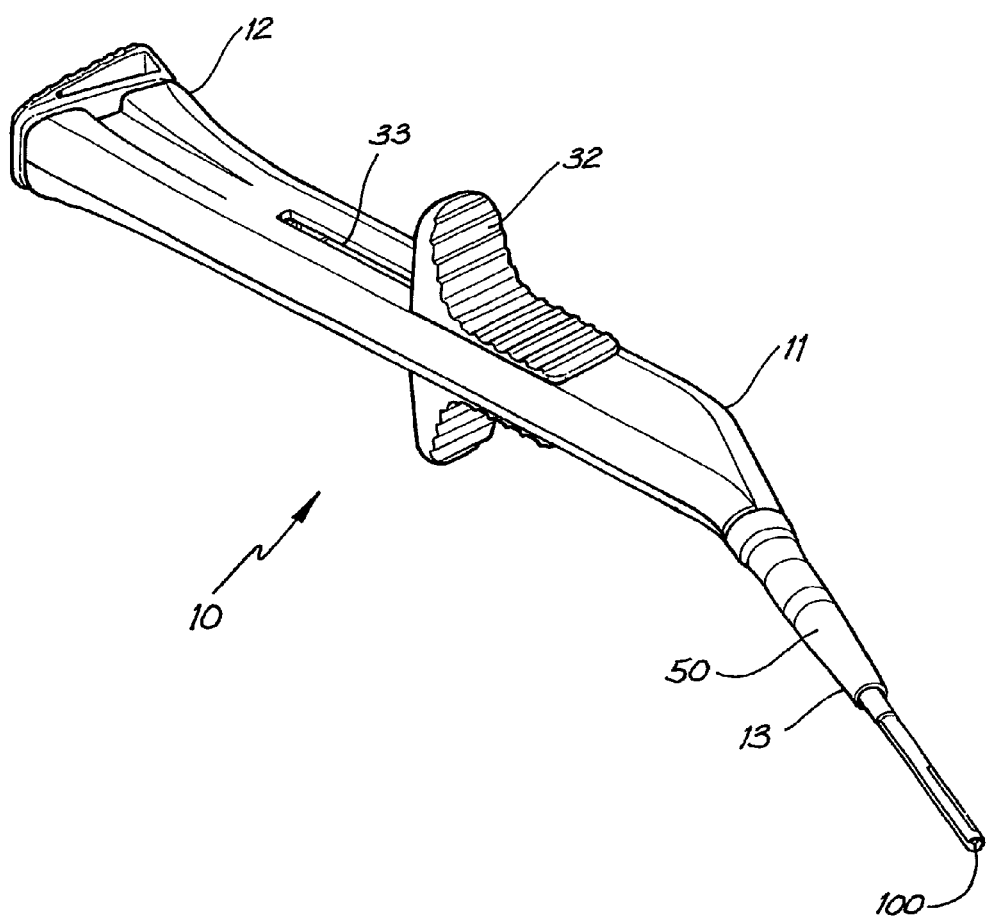
FIG. 1 is a schematic view of a fully assembled device according to a preferred embodiment of the present invention.

A device of one embodiment of the present invention is generally depicted as 10 in the accompanying drawings. The device 10 is used for inserting an electrode array 100 into a cochlea of a subject and removing a straightening member 101 of the electrode array 100.

The device comprises a housing 11 which extends from a proximal end 12 to a distal end 13. The distal end 13 is adapted to receive a portion of the electrode array 100.

The device further comprises an electrode array positioning member 14 which extends through the housing 11 from a first end 15 to a second end 16. The second end 16 engages part of the electrode array 100 such that movement of the electrode array positioning member 14 from a first position to a second position effects movement of the electrode array 100 from a first position substantially within the housing 11 to a second position substantially extending from the distal end 13 of the housing 11.

The device 10 also has a capture member 17 which extends through the housing 11 from one end 23 to a capture end 24. The capture end 24 engages a portion of the straightening member 101 of the electrode array 100 such that the straightening member 101 is restricted from moving with the electrode array 100 from its first position substantially within the housing 11 to its second position substantially extending from the distal end 13 of the housing 11.

The electrode array positioning member 14 includes a plunger 18 at its first end 15. When the device 10 is in use, a user exerts pressure on the plunger 18 to cause movement of the electrode array positioning member 14 from its first position to its second position, that is in a direction towards the distal end 13 of the housing 11. The plunger 18 includes a thumb rest 19 which is adapted to abut with the proximal end 12 of the housing 11. This abutment limits movement of the plunger 18 towards the distal end 13 of the housing 11 thus ensuring that a user does not advance the electrode array 100 to an undesirable depth into a cochlea of a subject.

Figure 3A:
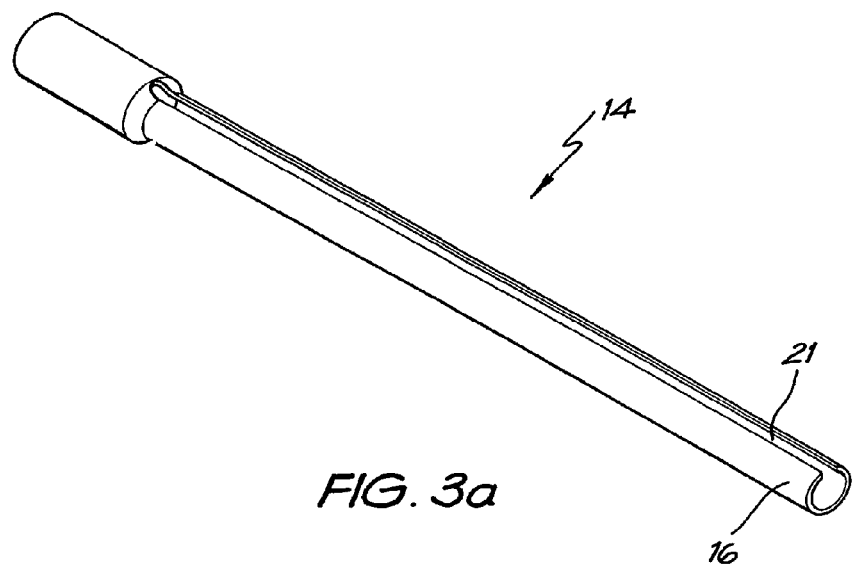
FIGS. 3a and 3b are schematic views of part of the electrode array positioning member of the device shown in FIG. 1.
Figure 3B:
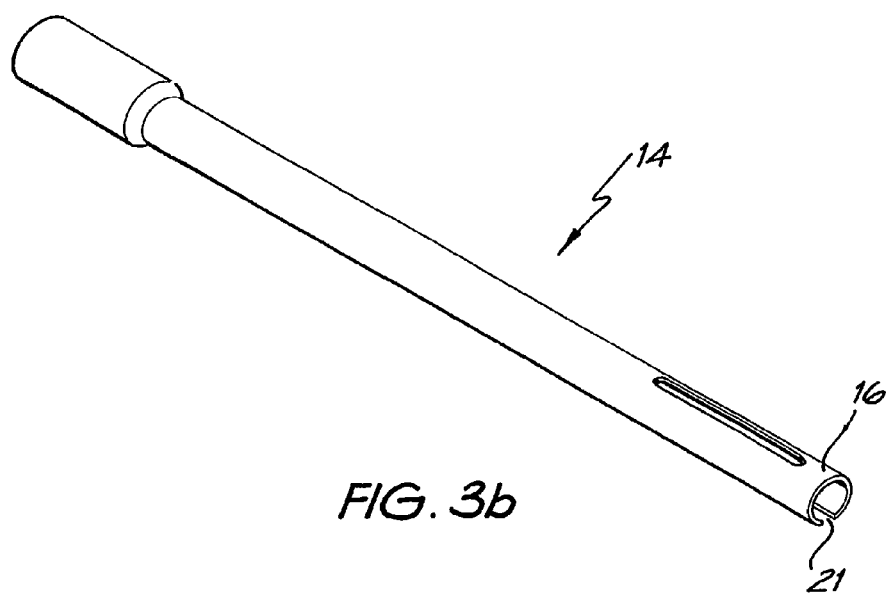

A region 21 of the electrode array positioning member 14 adjacent to the second end 16 is slotted as depicted in FIG. 3a. The slotted region 21 receives part of the straightening member 101 of the electrode array 100 as described in further detail below. The slotted region 21 may also include a window as depicted in FIG. 3b.

The slotted region 21 also receives a portion of the capture member 17.

The capture member 17 comprises an elongate member 22 which extends from the one end 23 to the capture end 24.

Figure 5:
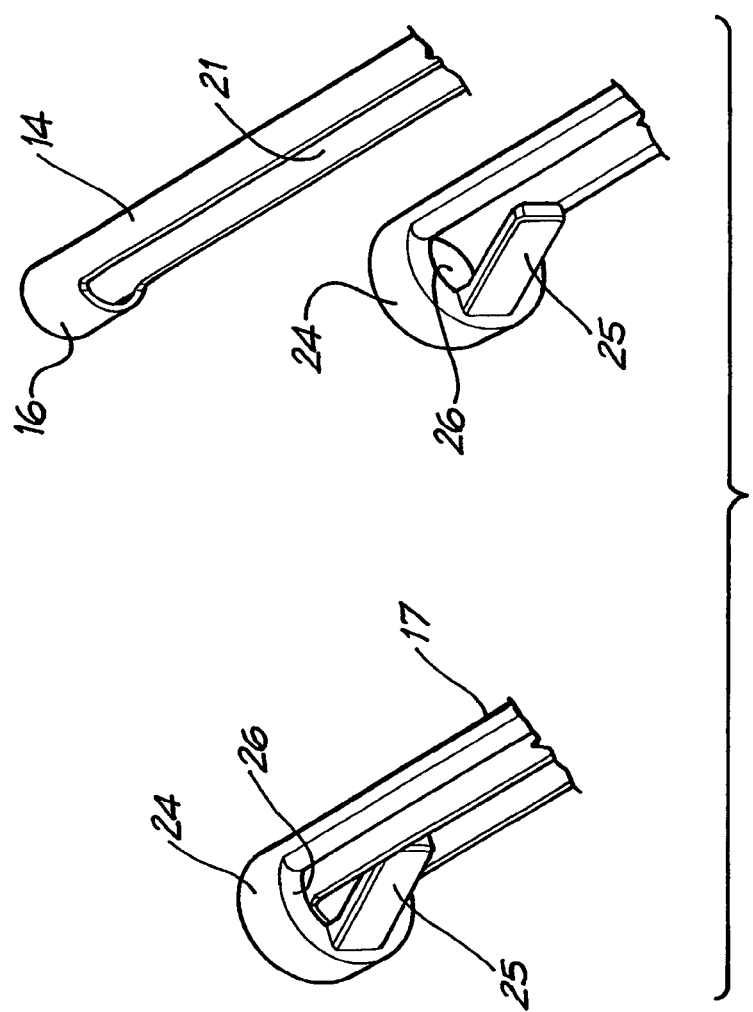
FIG. 5 shows schematic views of part of the capture member of the device of FIG. 1.

As shown in FIG. 5, the capture member 17 includes a flap member 25 located adjacent the capture end 24. The flap member 25 is adapted to engage part of the straightening member 101 of the electrode array 100 when said electrode array 100 is loaded onto the device 10.

Figure 2:
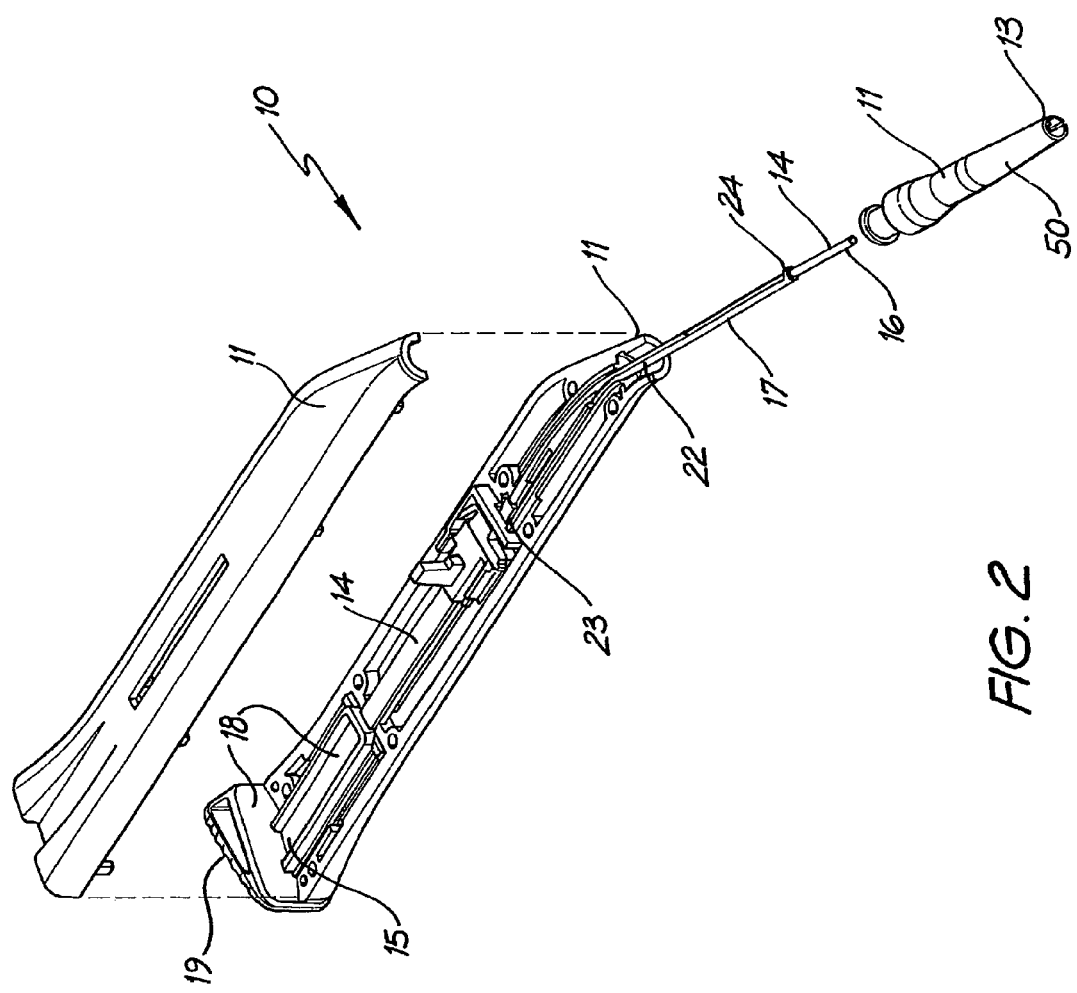
FIG. 2 is a schematic view of the partially assembled device of FIG. 1.
Figure 4:
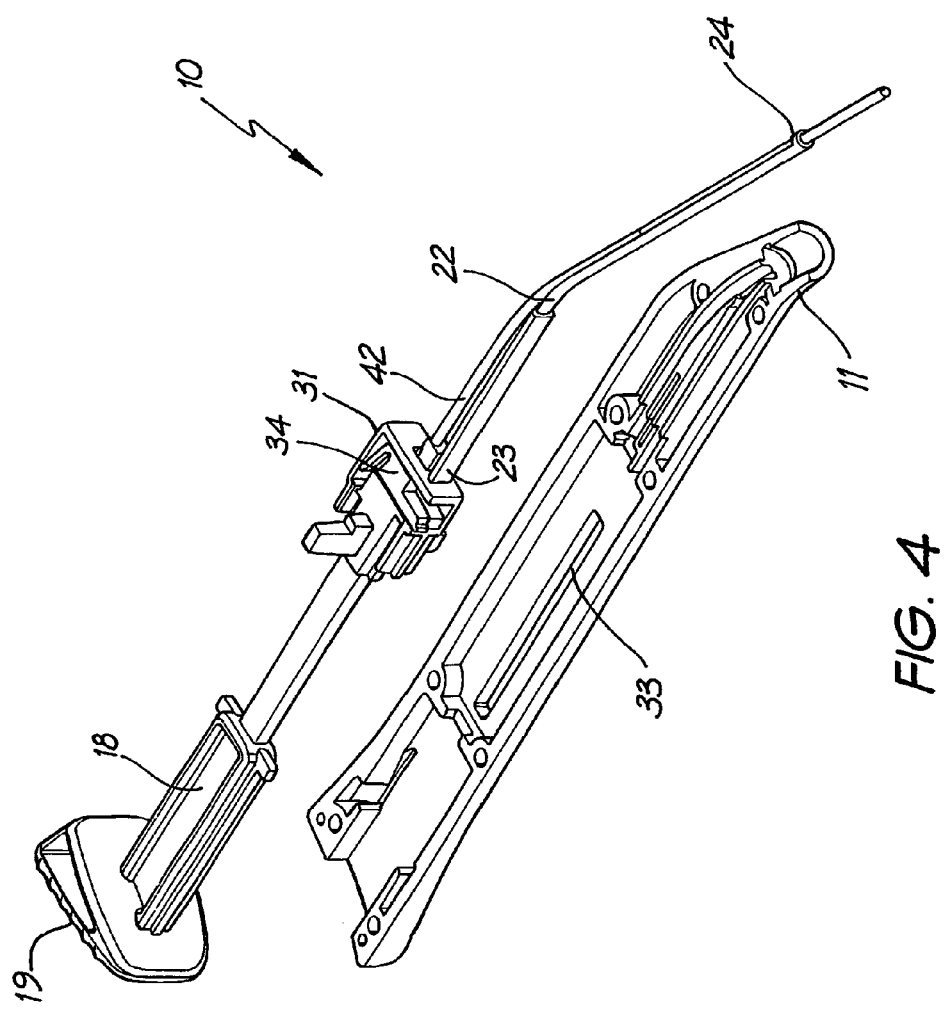
FIG. 4 is a further schematic view of the partially assembled device of FIG. 1.

As shown, the capture end 24 of the capture member 17 forms a hollow cylinder 26 which, when the device 10 is fully assembled, extends around the second end 16 or a portion adjacent thereto of the electrode array positioning member 14 (as shown in FIGS. 2 and 4). The flap member 25 extends from the capture end 24 and into the slotted region 21 of the electrode array positioning member 14.

The straightening member 101 of the electrode array 100 extends through a central lumen or along a slot in the electrode array (not shown) and an engagement portion 103 extends beyond the proximal end 102 of the electrode array 100. The straightening member 101 acts to straighten a pre-curved electrode array thus enabling insertion of the electrode array into the cochlea.

The engagement portion 103 of the straightening member 101 includes a ball member 104, a loop 105, an arrow member 106, a bullet member 107 or a hemispherical member 108. As depicted in FIGS. 6a to 6d, the engagement portion includes loop 105 in combination with any one of ball member 104, arrow member 106, bullet member 107 or hemispherical member 108. In this regard, loop 105 is located further from the electrode array 100 than either ball member 104, arrow member 106, bullet member 107 or hemispherical member 108. A surgeon may therefore maintain the option of inserting the electrode array 100 manually wherein the loop 105 may be more easily captured by a hand tool such as a hook, forceps, tweezers or the like. Rather than grasping the loop 105, it is possible to provide a surface 199 having a recess formed therein such that it may form a concave face which may be captured either by the capture member of the device or alternatively captured by a surgeon using a hand tool, such as a surgical pick.

Figure 6A:
FIGS. 6a-6f and 6j show part of a straightening member of an electrode array.
Figure 6B:
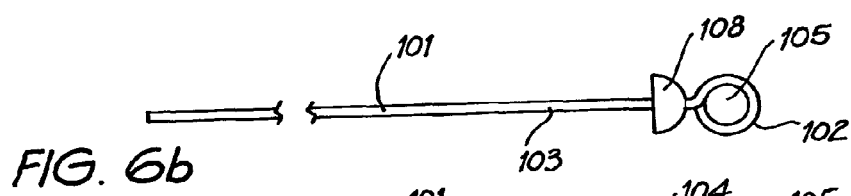
Figure 6C:
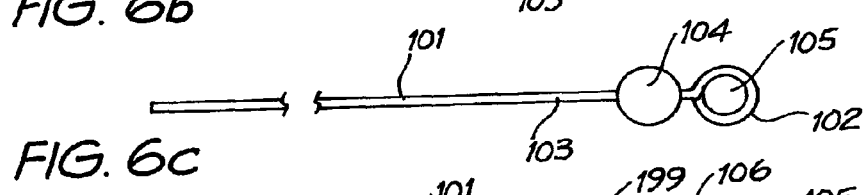
Figure 6D:
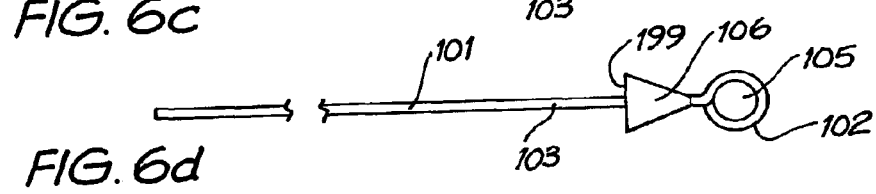
Figure 6E:
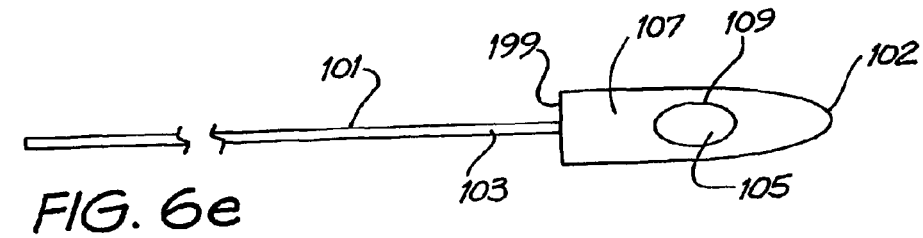
Figure 6F:
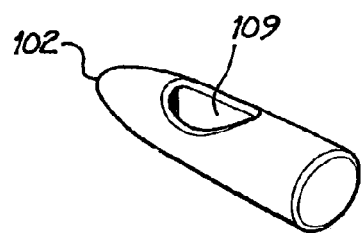
Figure 6J:
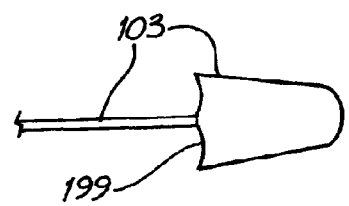

In FIGS. 6e and 6f, the loop 105 is formed from an aperture 109 in bullet member 107. The aperture 109 enables a surgeon to capture the straightening member 101 with a hand tool as mentioned above.

The electrode array 100 is loaded onto a cartridge member 29 with engagement portion 103 extending from one end of the cartridge member 29. The end of the cartridge member 29 with the engagement portion 103 extending therefrom is received within the distal end 13 of the housing 11. As the cartridge member 29 is loaded onto said distal end 13, the engagement portion 103 moves through the slotted region 21 of electrode array positioning member. 14. As discussed above, the flap member 25 of the capture member 17 extends into the slotted region 21.

If the flap member 25 is made from a resiliently flexible material, as the engagement portion 103 moves into and along the slotted region 21 of the electrode array positioning member 14, the flap member 25 is deformed by the engagement portion 103 as it passes said flap member 25. Once the engagement portion 103 has moved beyond the flap member 25, the flap member 25 resumes its original configuration, that is, extending through the slot of the slotted region 21 of the electrode array positioning member 14.

The positioning of the flap member 25 extending through the slot of the slotted region 21 prevents any further movement of the engagement portion 103 in the reverse direction, that is, towards the second end 16 of the electrode array positioning member 14.

Figure 6G:
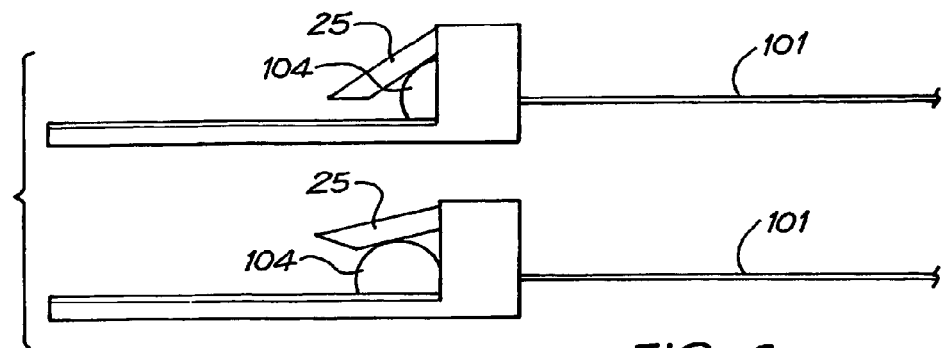
FIGS. 6g, 6h, and 6i depict part of the straightening member being captured by an embodiment of a capture member of the device of the present invention.
Figure 6H:
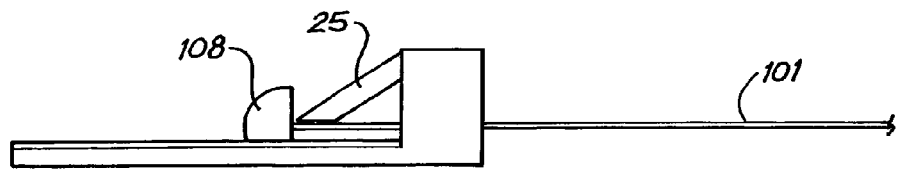
Figure 6I:
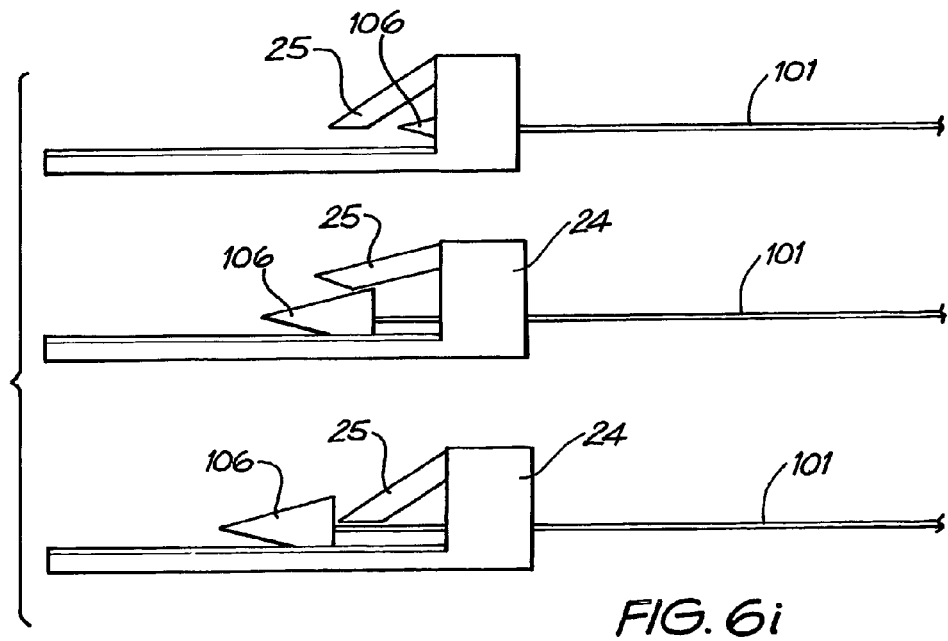

FIGS. 6g to 6i show the engagement portion 103 passing the flap member 25. In FIG. 6g, the engagement portion 103 includes ball member 104 whereas in FIG. 6h, the engagement portion 103 includes a hemispherical member 108.

The engagement portion 103 shown in FIG. 6i includes an arrow member 106 which has the advantage that it is has a gradual and longer taper than the ball 104 or the hemisphere 108.

With the electrode array 100 loaded onto the device 10, the second end 16 of the electrode array positioning member 14 abuts with a proximal end 102 of the electrode array 100. The engagement portion 103 extends into the slotted region 21 of the positioning member 14 and is held within the slotted region 21 by the flap member 25.

When the plunger 18 of the electrode array positioning member 14 is moved in a direction towards the distal end 13 of the housing, the second end 16 of the electrode array positioning member 14 pushes the proximal end 102 of the electrode array 100 such that the electrode array 100 is advanced from the distal end 13 of the housing 11, and when used in a surgical procedure, advanced into a cochlea of a subject.

As the electrode array 100 is advanced into the cochlea, as detailed above, the engagement portion-103 of the straightening member 101 is held by the flap member. 25 of the capture member 17 and therefore the straightening member 101 is restricted from advancing into the cochlea with the electrode array 100. There may be some advancement of the straightening member 101 with the electrode array 100, however such advancement will only be relatively minimal until the flap member 25 captures the engagement portion 103 of the of the straightening member 101. Accordingly, the electrode array 100 advances off the straightening member 101 and into the cochlea. Substantially free of the straightening member 101, the electrode array 100 may then start to take on a pre-curved configuration within the cochlea of the subject, allowing the electrode array to assume a mid scala trajectory into the cochlea which reduces the reliance on the sensitive structures of the walls of the cochlea to guide the electrode array into the cochlea. As a result, this provides a more efficient, safer, less traumatic, and potentially deeper electrode array insertion procedure.

To fully remove the straightening member 101 from the electrode array 100, the capture member 17 is moved in a direction towards the proximal end 12 of the housing 11. Such movement causes the flap member 25 of the capture member 17 to abut with the engagement portion 103 of the straightening member 101 and pull said engagement portion 103 along the slotted region 21 of the electrode array positioning member 14 in a direction towards the proximal end 12 of the housing 11.

The one end 23 of the capture member 17 is connected to a slide member 31, which when the device is fully assembled, is located within the housing 11. The slide member 31 includes two fingers rests 32 which extend from the slide member 31 through two opposing slots 33 in the wall of the housing 11. A user moves the finger rests 32 along the slots 33 to effect movement of the capture member 17. Movement of the finger rests 32 in a direction towards the proximal end 12 of the housing 11 will effect full withdrawal of the straightening member 101 from the electrode array 100.

The device 10 further comprises a safety mechanism to prevent withdrawal of the straightening member 101 before the electrode array positioning member 14 has moved to its second position and the electrode array 100 advanced into the cochlea of a subject. In this regard, the slide member 31 further includes a spring member 34 which is housed within a recess in the slide member. The spring member 34 is made from a resiliently flexible material and includes "a main body 35 which on one side 36 is hingedly connected to a leg member 37. On an opposing side 38 of the main body 35, the spring member 34 includes a housing engagement portion 39 which extends from the main body 35 and into a niche (not shown) in the inner wall of the housing 11 of the device 10. When the housing engagement portion 39 is positioned within the niche of the housing 11, any movement of the spring member in either a direction towards the distal end 13 or the proximal end 12 of the housing 11 is prevented. As the spring member 34 is housed within the slide member 31, the slide member 31 and the capture member 17 (which is connected to said slide member 31) are prevented from moving in either direction.

The slide member 31 and the main body 35 of the spring member 34 further include a groove 40 which receives a portion of the electrode array positioning member 14 and allows the electrode array positioning member to pass therethrough.

The electrode array positioning member 14 comprises a number of components connected to or integral with one another. The plunger member 18 comprises a thumb rest 19 connected to or integral with a pushing arm 41. The pushing arm 41 is connected to or integral with an intermediate member 42 which has a smaller cross-sectional diameter than the pushing arm 41. Finally, the intermediate member 42 is connected to or integral with an end member 43.

The end of the pushing arm 41 which is connected to the intermediate member 42 is slightly tapered in its join with the intermediate member 42. Accordingly, said end of the pushing arm 41 which joins with the intermediate member 42 forms a shoulder 44.

In use, the intermediate member 42 passes through the groove 40 of the slide member 31 and the spring member 34 when the plunger 18 is actuated and the electrode array 100 advanced into a cochlea. Movement of the intermediate member 42 through the groove 40 does not disrupt the configuration of the spring member 34. Accordingly, if the spring member 34 is positioned such that the housing engagement member 39 is within the niche in the housing 11, movement of the intermediate member 42 through the groove 40 does not dislodge the housing engagement member 39 and thus the spring member 34, slide member 31 and capture member 17 are fixed in position relative to the housing 11. This enables the electrode array positioning member 14 to be moved to its second position without the straightening member 101 of the electrode array 100 being withdrawn prematurely from said array.

As the electrode array positioning member 14 reaches its second position, the tapered end of the pushing arm extends into the groove 40 until the shoulder 44 of the pushing arm 41 pushes against a wall of the groove 40 of the main body 34. This causes the main body 34 to move about its hinged joint with the leg member 37 from a first position wherein the main body 34 is relatively spaced from the leg member 37 to a second position wherein said main body 34 is relatively less spaced from the leg member 37. Such movement of the main body 34 of the spring member 34 disengages the housing engagement member 39 from the niche in the inner wall of the housing 11. With the housing engagement member 39 disengaged from the inner wall of the housing 11, the slide member 31 and the capture member 17 are free to be moved by way of the finger rests 32 in a direction towards the proximal end 12 of the housing 11.

The housing 11 is tapered towards the distal end 13 to form a tip member 50 suitable for introduction into a patient. The tip member 50 may be integral with the remainder of the housing 11 or may in the alternative be detachable from the remainder of the housing 11-11^—shown in FIG. 2.

Further, the tip member 50 is angled relative to the remainder of the housing 11 to provide a good line of vision for a surgeon during insertion of the electrode array 100. The electrode array positioning member 14 and the capture member 17 are also angled along their length to correspond with the angled structure of the housing 11.

Figure 7:
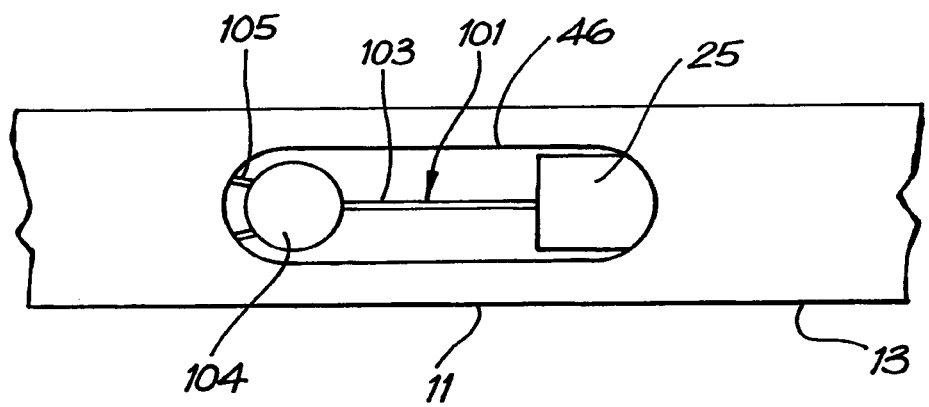
FIG. 7 is a view through a window of the device depicted in FIG. 1.
Figure 8:
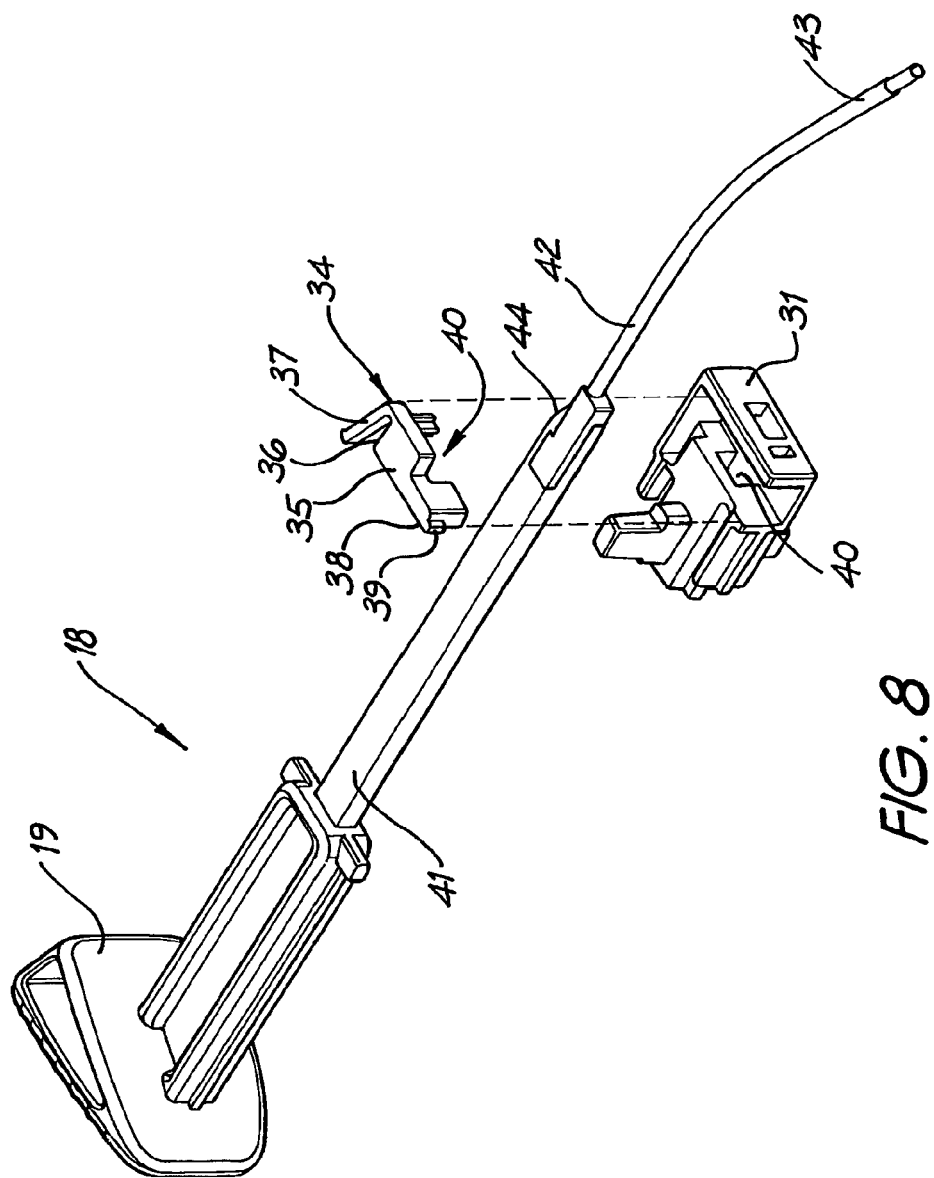
FIG. 8 is a further schematic part view of the device of FIG. 1.

The tip member 50 of the housing 11 includes a window 46 to allow a user to view the electrode array 100 once said array is loaded onto the device 10. If loaded correctly, the user should be able to view the engagement portion 103 of the straightening member 101 through the window as shown in FIG. 7.

Figures 9A, 9B:
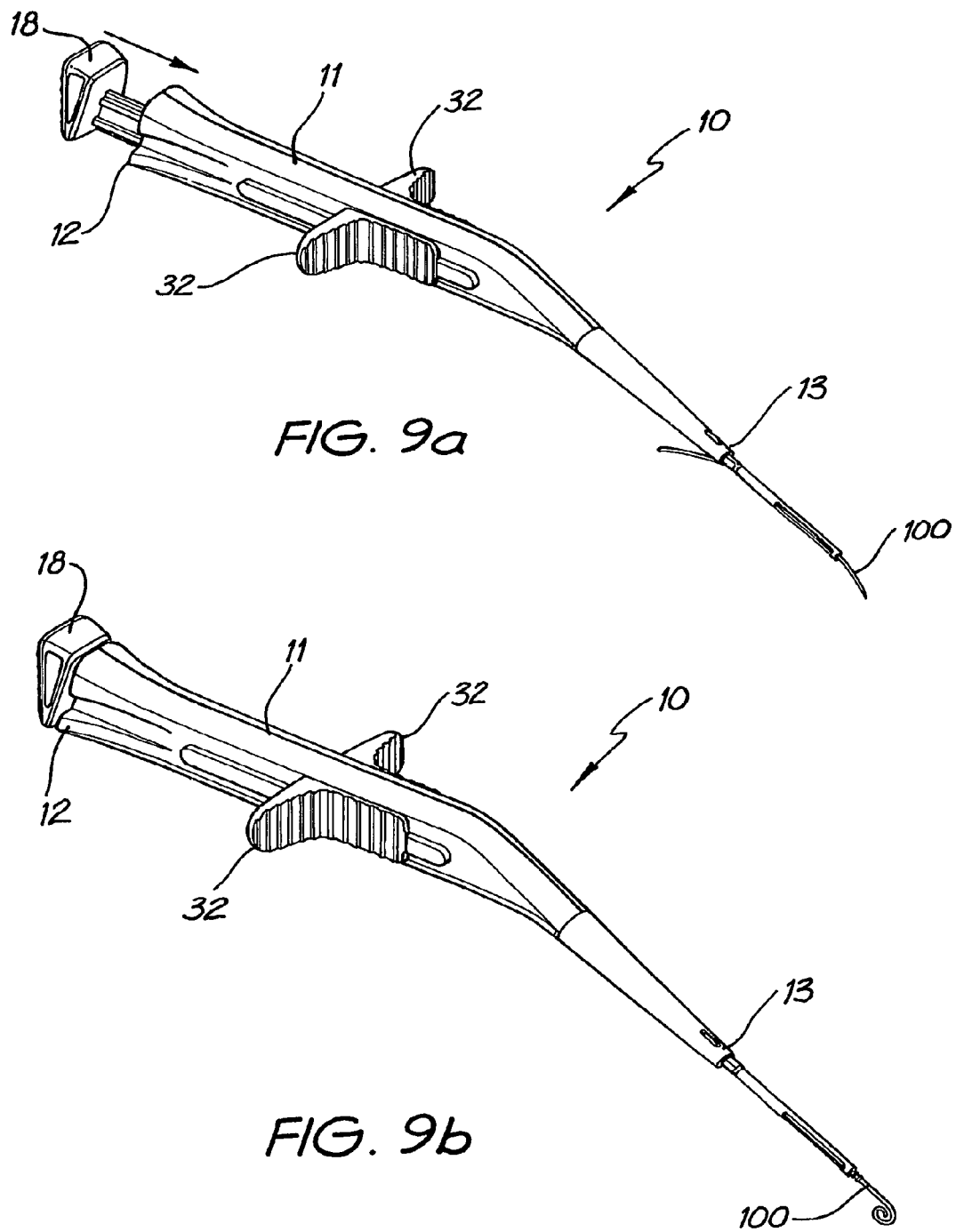
FIGS. 9a, 9b and 9c show the device of FIG. 1 during the various stages of insertion of an electrode array.
Figure 9C:
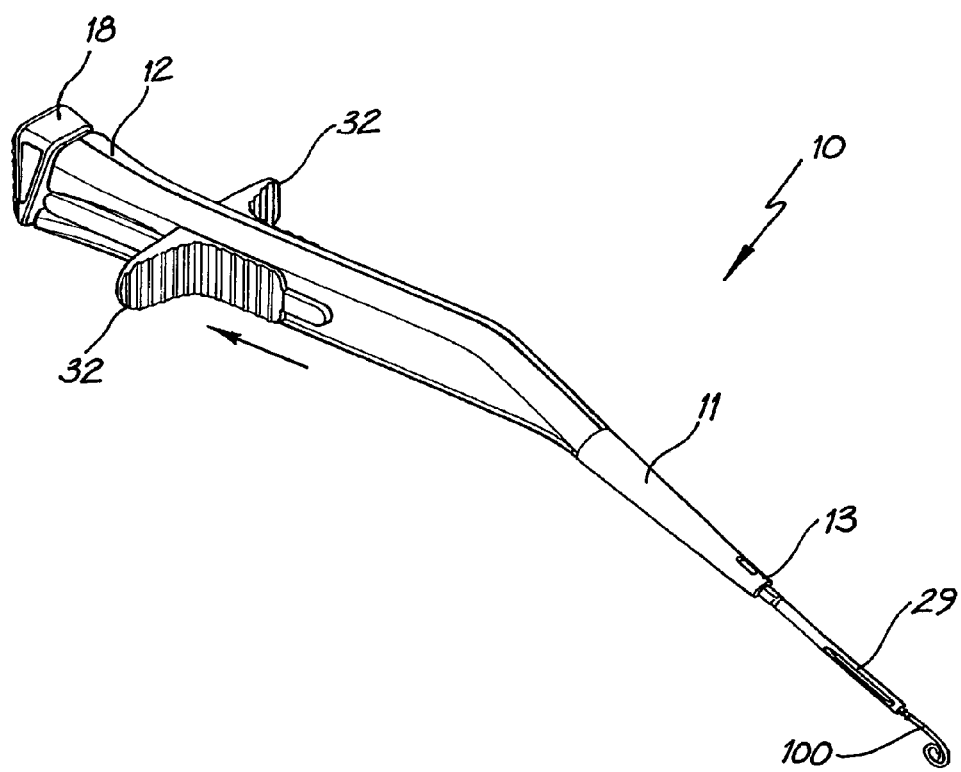

FIGS. 9a, 9b and 9c show the device during the various stages of a surgical procedure. The plunger 18 is steadily moved towards the proximal end 12 of the housing 11 until it abuts with the proximal end 12 and cannot be moved any further. As depicted, the movement of the plunger 18 advances the electrode array 100 from the distal end 13 of the housing 11. As the straightening member 101 is held by the capture member 17 of the device 10, the electrode array 100 advances off the straightening member and from the housing 11, whereupon it takes on a pre-determined—curved configuration. The finger rests 32 may then be drawn back towards the proximal end 12 of the housing 11 such that the straightening member 101 is fully removed from the electrode array 100.

A cartridge member as defined in the third aspect of the invention is generally depicted as 129 in the accompanying drawings. The cartridge member 129 is shown when used with electrode array 100 which has straightening member 101 extending therefrom.

Figure 10A:
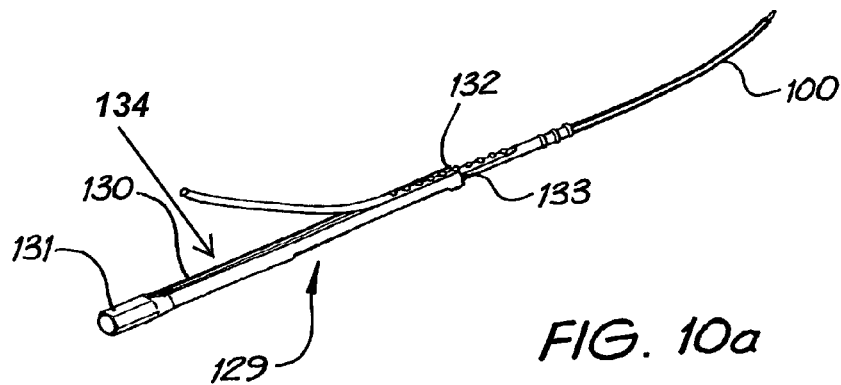
FIGS. 10a, 10b and 10c show a cartridge member according to another aspect of the invention.
Figure 10B:
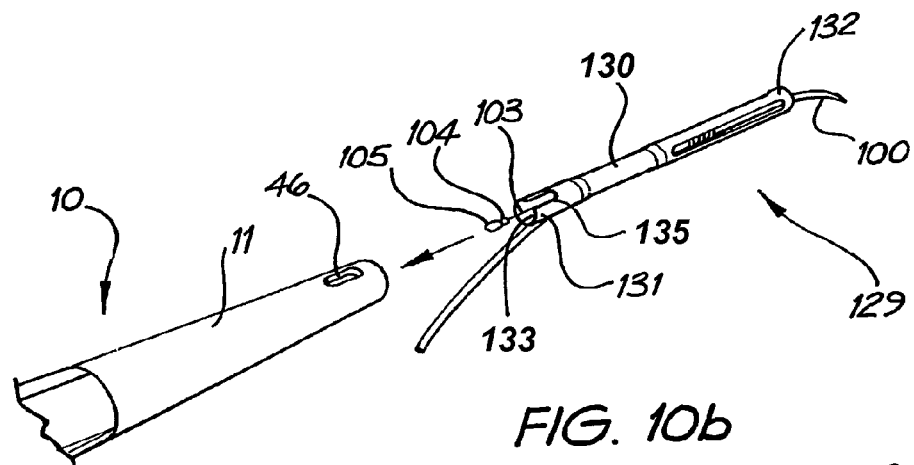
Figure 10C:
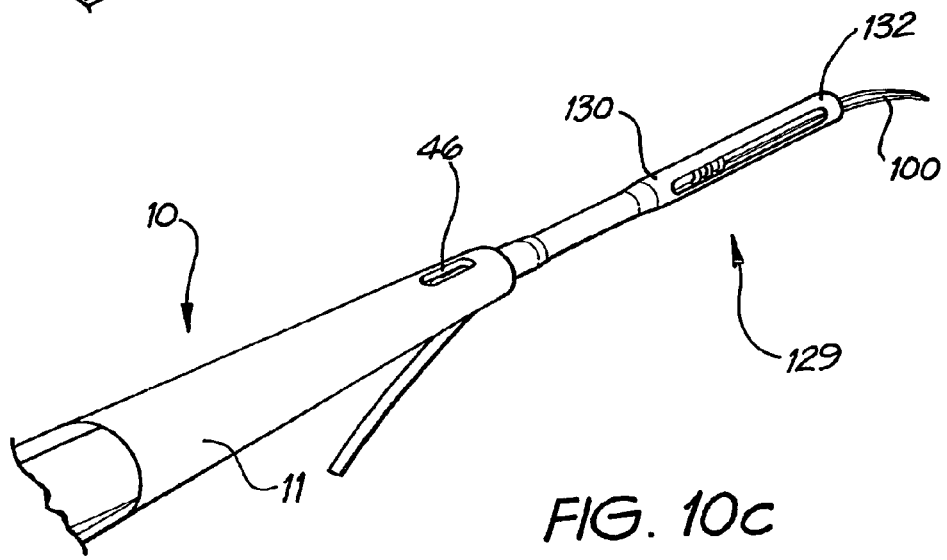

As depicted in FIGS. 10a, 10b and 10c, the cartridge member 129 includes an elongate body 130 which extends from a first end 131 to a second end 132. The elongate body 130 has an internal lumen 133 which extends therethrough and which is adapted to receive the electrode array 100.

The cartridge member 129 further includes a slot 134 along a portion of the length of the elongate body to accommodate the electrical leads of the electrode array 100 and a window 135 in a portion of the sidewall of the elongate body 130 adjacent the first end 131. The window 135 enables a user to view a portion of the electrode array 100 which is positioned within the lumen 133 of the cartridge member 129.

The electrode array 100 is loaded onto the cartridge member 129 by feeding the engagement portion 103 of the straightening member 101 of the electrode array 100 into the second end 132 of the cartridge member. The electrode array 100 is oriented such that the electrical leads of the electrode array 100 are substantially aligned with the slot 134 along the elongate body 130 of the cartridge member 129. The electrode array 100 is then guided into the cartridge member 129 by pulling lightly on the electrical leads of the electrode array 100 until the ball 104 and loop 105 extend from the first end 131 of the cartridge member 129.

The cartridge member 129 and electrode array 100 may be used with device 10 as depicted in FIGS. 10b and 10c. The cartridge member 129 is loaded onto the distal end 13 of the housing 11 and the electrode array positioning member 14 of the device 10 caused to engage the electrode array 100 within the cartridge member 129.

As mentioned above, a portion of the housing 11 adjacent the distal end 13 includes a window 46. As the cartridge member 129 is loaded onto the device 10, the window 135 of the cartridge member 129 is aligned with the window 46 in the housing 11 of the device 10.

FIGS. 11a to 11d show a further embodiment of device 10 of the present invention wherein the electrode array positioning member 14 comprises an elongate member extending from first end 15 to second end 16. Second end 16 is forked to maximize engagement with electrode array 100. In this embodiment, the positioning member includes a plunger 18 at its first end 15. Movement of the plunger 18 in the direction shown by the arrow in FIG. 11d causes the electrode array 100 to move from the distal end of the housing 11 and into a cochlea of a patient.

The capture member 17 of this embodiment comprises a tie member 150 which is anchored at one end 151 to an anchor 152 located on a wall of the housing 11. At its second end 153 the tie member 150 engages the engagement portion 103 of straightening member 101. In this case, the tie member forms a loop at the second end 153 to engage a complementary part of the engagement portion.

As the housing 11 of this embodiment remains relatively fixed in the forward direction during the insertion procedure, as the electrode array is advanced into the cochlea, the engagement portion 103 of the straightening member is held by the tie member 150 and thus the electrode array 100 advances off the straightening member 101.

This embodiment has a number of safety features including a cochleostomy stopper 154 positioned adjacent the distal end 13 of the housing 11. During an insertion procedure, the cochleostomy stopper 154 abuts with an edge of a cochleostomy such that the housing 11 is prevented from advancing too far into a cochlea of a subject.

Other safety features include a means to prevent the electrode array 100 from advancing too far into a cochlea of a subject thereby damaging the surrounding tissue. In this regard, the electrode array positioning member 14 includes a second stopper 155 located at a position along its length. The second stopper 155 abuts with a portion of the housing 11 such that the electrode array positioning member 14 is prevented from moving any further in a direction towards the distal end 13 of the housing 11.

A further embodiment of device 10 is depicted in FIGS. 12, 12a, 12b, 13, 13a and 13b. The housing 11 comprises a handle 160 and a tip member 161. The tip member 161 includes the electrode array positioning member 14 which comprises an inner member 162 which is slidably receivable within an outer member 163. The inner member 162 comprises an elongate tubular structure extending from a first end 164 connected to the handle 160 to a second end 165 adapted to receive electrode array 100. The tubular structure of the inner member 162 defines an internal lumen 159 extending therethrough.

The outer member 163 also comprises a tubular structure defining an internal lumen 170. The outer member 163 extends from a proximal end 166 relatively adjacent the handle 160 to a distal end 167 relatively distal the handle 160. The outer member 163 further includes capture member 17 positioned along the length of the outer member 163.

The handle 160 comprises a plunger member 168 which, when the device is in use, is moved forward relative to the outer member 163 and in a direction towards the cochlea (not depicted) of the subject. As the inner member 162 is connected to the handle 160, such movement causes the inner member 162 to move longitudinally forward relative to the outer member 163 until at least part of the inner member extends beyond the distal end 167 of the outer member 163. This action advances the electrode array 100 forward of the outer member 163 and into the cochlea.

Figure 12:
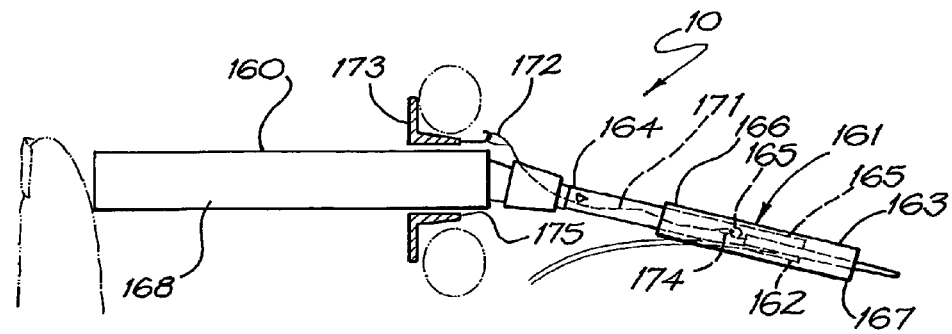
Figure 12A:
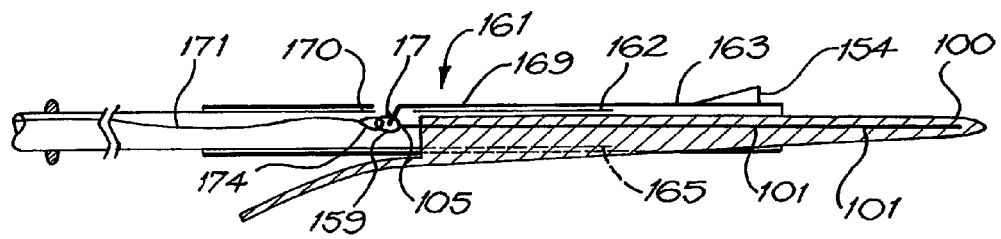
Figure 12B:
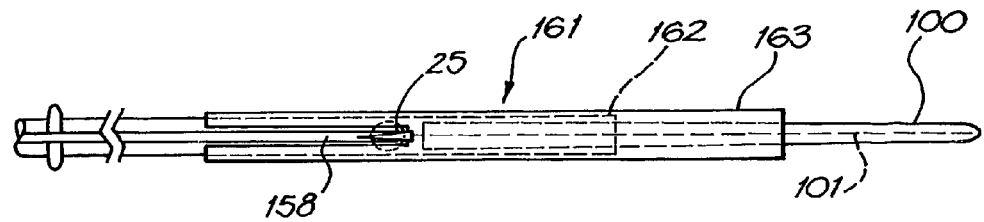
Figure 13:
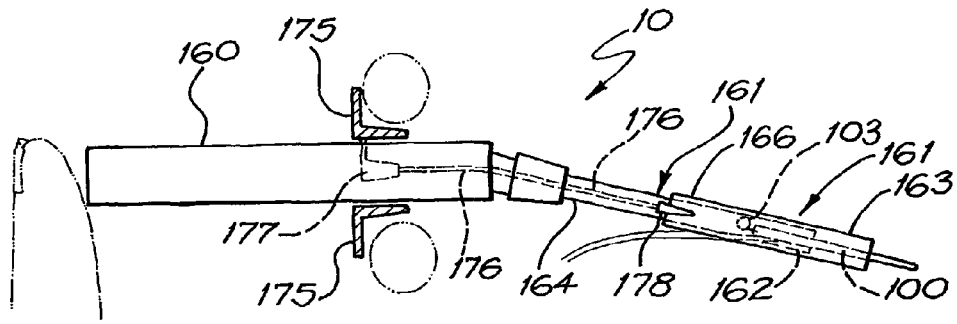
Figure 13A:
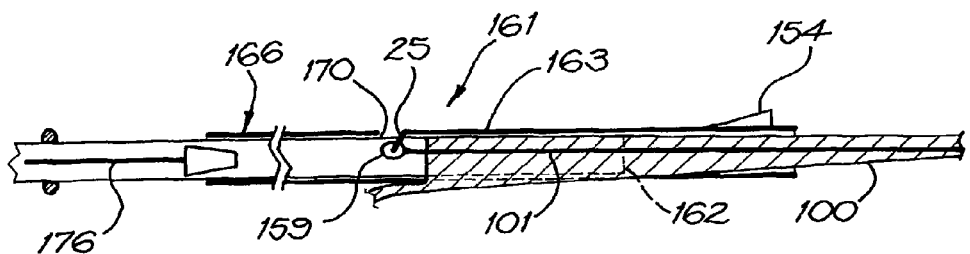

The outer member 163 includes a cochleostomy stopper 154 as depicted in FIGS. 12a and 13a. The cochleostomy stopper 154 is located adjacent the distal end 167 of the outer member 163. In use, the cochleostomy stopper 154 abuts with the edge of a cochleostomy (not shown) thereby preventing the outer member 163 from moving into the cochlea. In this way, the outer member 163 is substantially fixed in a position and cannot move further into the cochlea during use of the device 10.

The capture member 17 comprises a flap member 25 as depicted in FIGS. 12a, 12b, 13a and 13b. The flap member 25 extends from a wall 169 of the outer member into the lumen 170 of the tubular outer member 163 and through a slot 158 in the wall of the inner member 162 such that it extends into lumen 159 of the inner member 162.

In this embodiment, the engagement portion 103 of the straightening member 101 of the electrode array 100 is depicted as a loop 105 which is engaged by flap member 25.

To fully remove the straightening member 101 from the electrode array 100, the device 10 may further include a tie line 171. The tie line 171 is connected at a first end 172 to an actuator member 173 located on handle 160. At a second end 174, the tie line 171 is connected to loop 105 of straightening member 101.

The tie line 171 is a flexible cord made from a suture-type material. Such 5 material has the advantage that it is biocompatible.

The actuator member 173 is a sliding means 175 which is movable along a length of the handle 160.

As the sliding means 175 is pulled back away from the surgical site, the tie line 171 is pulled taut such that the straightening member 101 together with the outer member 163 (as the outer member is in engagement with the straightening member via the capture member) are pulled away from a cochleostomy thereby fully withdrawing the straightening member 101 from the electrode array 100.

Figure 13B:
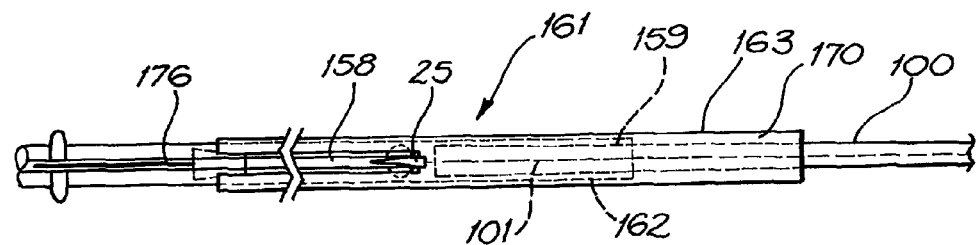

In the embodiment of the invention depicted in FIGS. 13, 13a and 13b, the device 10 includes a pulling rod 176 which is connected at one end 177 to the sliding means 175 and connected at a second end 178 to the proximal end 166 of the outer member 163. Movement of the sliding means 175 in a direction away from a surgical site causes the outer member 163 to withdraw from the cochleostomy site. As the capture member 17 of the outer member 163 is in engagement with engagement portion 103 of straightening member 101, movement of the sliding means 175 in this manner fully withdraws the straightening member 101 from the electrode array 100.

Figure 14:
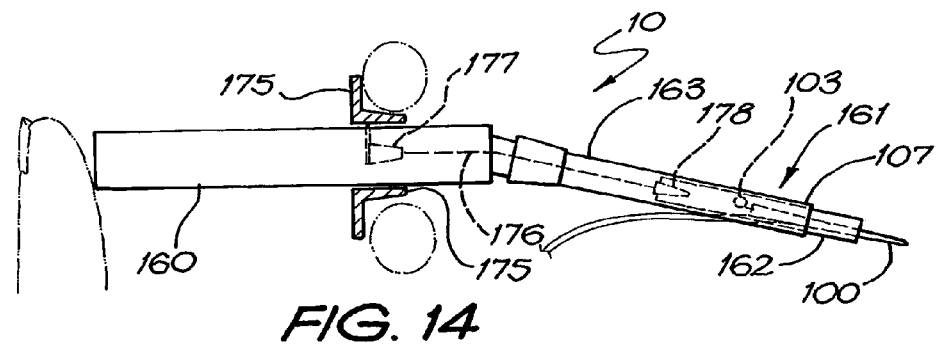
Figure 14A:
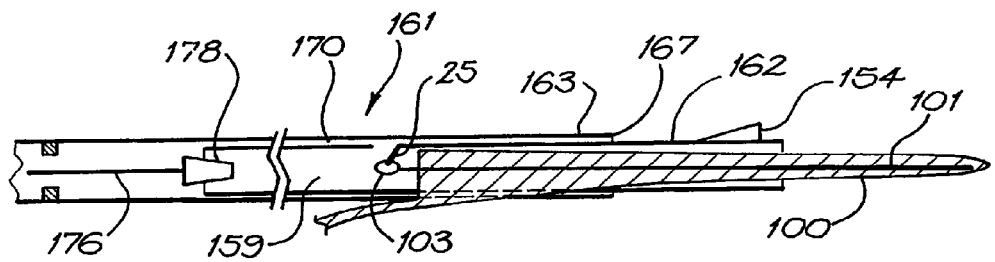
Figure 14B:
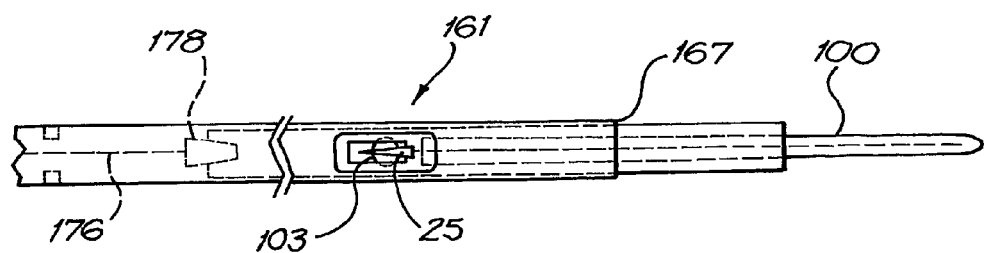

In the embodiment of the invention depicted in FIG. 14, the outer member 163 comprises the electrode array positioning member 14 which is connected to plunger member 168. The inner member 162 includes the capture member 17 ie flap member 25 on a wall of the inner member and extending into lumen 159 of inner member 162.

Figure 15:
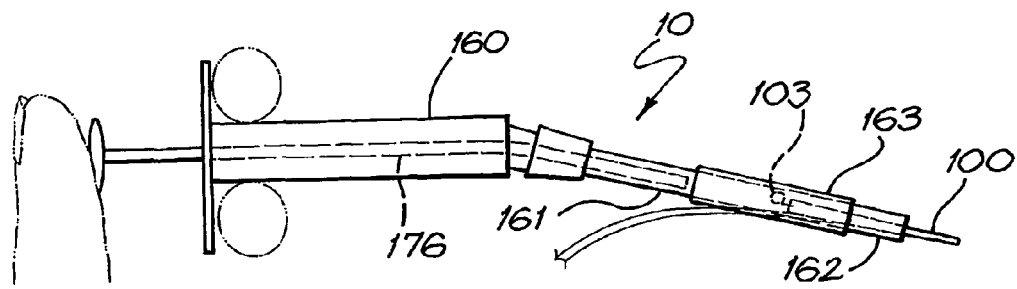
Figure 15A:
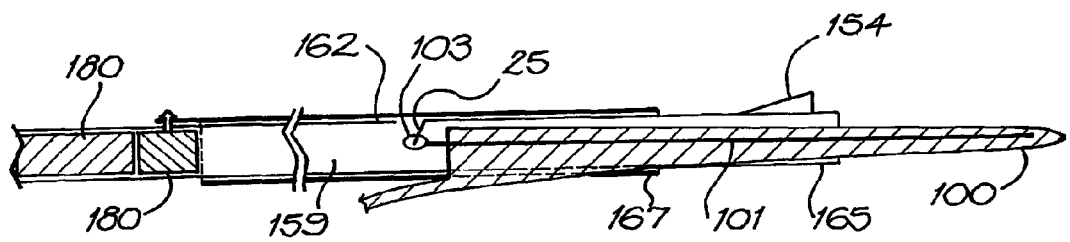
Figure 15B:
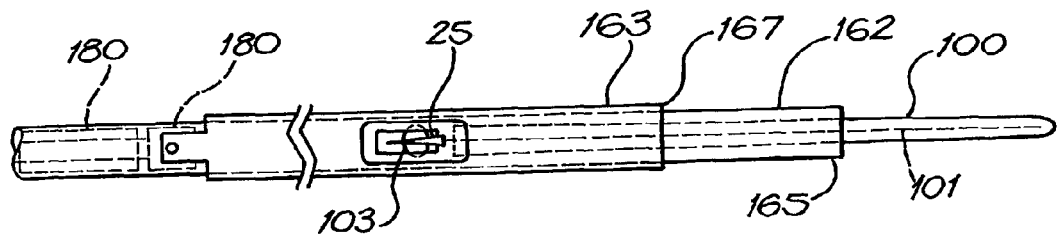

Movement of plunger member 168 causes movement of the outer member 163 relatively towards a surgical site such that the electrode array 100 is advanced into a cochlea of a subject. The outer member 163 may be directly connected to the handle 160 as depicted in FIG. 14 or, alternatively connected to the handle by a piston member 180 as depicted in FIGS. 15, 15a and 15b.

The pulling rod 176 is connected at its second end 174 to the first end 164 of the inner member 162. Movement of the sliding means 175 in a direction away from a surgical site causes the inner member to move away from the surgical site thereby fully withdrawing the straightening member 101 from the electrode array 100.

Figure 17:
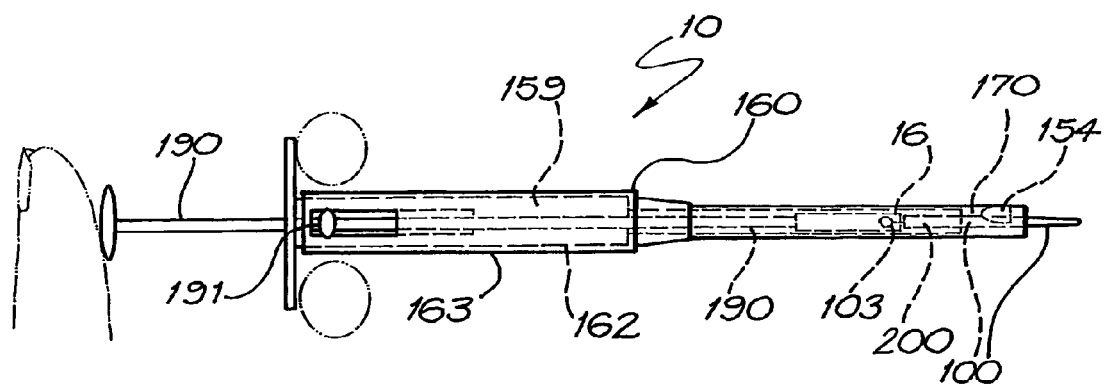
Figure 17A:
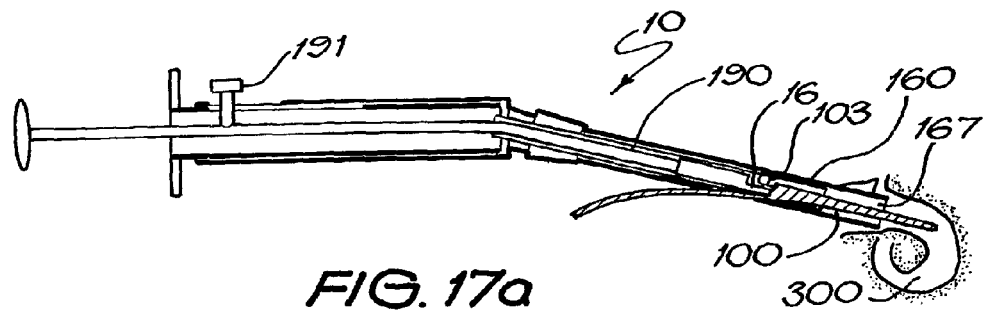
Figure 17B:
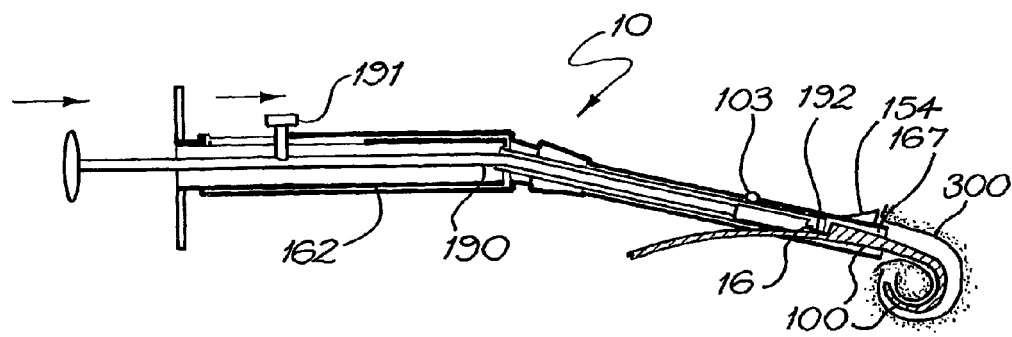
Figure 17C:
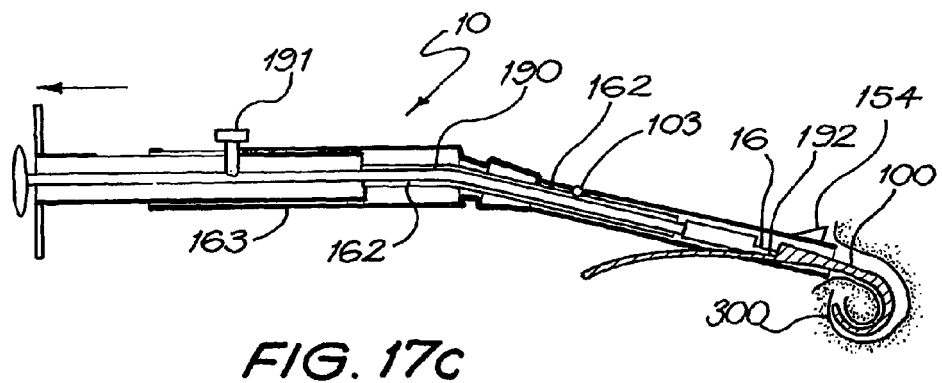

The device shown in FIGS. 17 and 17a, b and c has a housing 11 which comprises an inner member 162 and an outer member 163. The inner member is received within lumen 170 of the outer member 163. The electrode array positioning member 14 in this embodiment may be seen as an elongate pushing rod 190 which extends through lumen 159 of inner member 162, along a substantially length of the inner member 162.

The inner member 162 includes the capture member which typically comprises flap member 25 extending from a wall of the inner member 162 and into the lumen 159 of inner member 162. The capture member engages engagement portion 103 of the straightening member which extends into the lumen 159 at the second end 165 of the inner member 162 when an electrode array is loaded onto the device.

The electrode array is advanced into the cochlea 300 during a procedure by pushing plunger 18. As the electrode array positioning member advances towards the cochlea 300 of a subject, the inner member 162 is held in a relatively fixed manner such that it cannot move in said forward direction. The electrode array 100 therefore advances off the straightening member 101. Alternatively or in addition to, the electrode array positioning member 14 may include an actuator member 191. The actuator member 191 extends from the elongate pushing rod 190 and through slots in the walls of the both the inner member 162 and the outer member 163. The actuator member 191 may be moved along said slots to actuate movement of the electrode array positioning member 14.

Figure 18A:
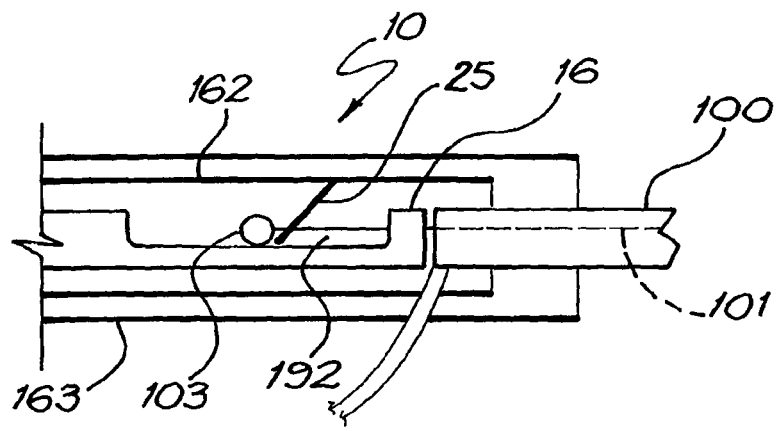
Figure 18B:
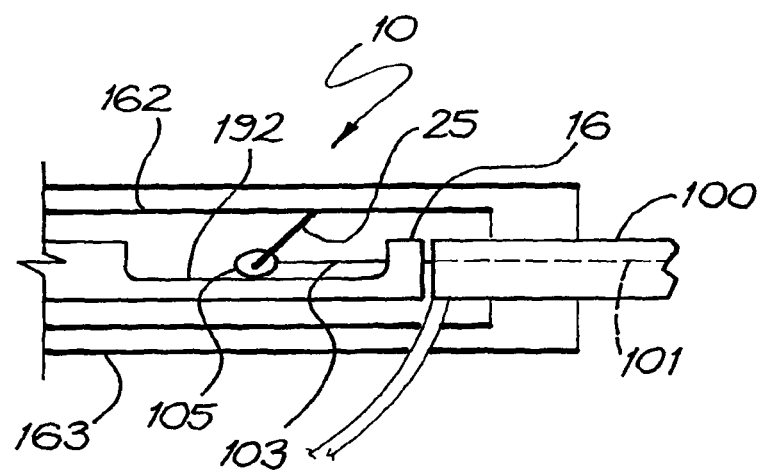

As depicted in FIGS. 18a and 18b, the second end 16 of the electrode array positioning member 14 includes a recessed portion 192 to accommodate engagement portion 103 of the straightening member 101. In this regard, the electrode array loaded on the device 10 may be moved by pushing the pushing rod against a proximal end 200 of the electrode array rather than pushing against engagement portion 103. This prevents damage to the engagement portion 103 which is housed in said recessed portion 192.

The embodiment of the invention depicted in FIGS. 19, 19a and 19b show how the elongate pushing rod 192 may be moved by movement of the actuator member 191. Rather than being connected to or forming part of the elongate pushing rod 190, the actuator member is brought into engagement with a proximal end 193 of the pushing rod 190.

The actuator member is a slide which may move along slots in the inner and the outer members. The actuator member 191 further includes an extension member 194. When the pushing rod 190 is in its second position, the extension member 194 abuts with a wedge 195 that inwardly extends from a wall of the inner member 162 and into lumen 159 of inner member 162. The extension member 194 is relatively rigid in structure and when the actuator member 191 is withdrawn from the surgical site, the extension member 194 exerts pressure on the wedge member 195 thereby causing the inner member 162 to also move in a direction away from the surgical site. As the inner member 162 includes the capture member 17, such movement allows full withdrawal of the straightening member 101 of an electrode array 100.

In the embodiment of the invention depicted in FIGS. 20 and 20a, the capture member 17 includes a pair of jaw members 200 at its capture end 24. The jaw members 200 are made from a suitably malleable material to allow movement of said jaw members 200 from a first open position (shown in FIG. 20) to a second closed position (shown in FIG. 20a). The jaw members 200 are moved to their closed position by movement of the electrode array positioning member 14 which in this embodiment comprises inner member 162. In this regard, the jaw members 200 may be held by elongate member 201 which extends through lumen 159 of inner member 162. The jaw members 200 extend from the second end 165 of the inner member 162 and flare outwardly from said second end 165. Movement of the inner member 162 by actuator member 191 causes the second end 165 of the inner member 162 to abut with the flared out jaw members 200.

The continued force applied to the jaw members 200 as the inner member 162 moves from its first to its second position causes said jaw members 200 to deform and take on their second closed position thereby capturing the engagement portion 103 of the straightening member of an electrode array 100 loaded onto the device 10.

The capture member is prevented from moving in the direction of the inner member 162 by stopper member 204 which abuts with a shoulder 205 of a recessed section 206 of the capture member 17.

The capture member 17 of this embodiment further includes a latch member 202 which engages actuator member 191 when the inner member 162 is in its second position. By moving the actuator member 191 in a reverse direction, away from a surgical site, said actuator member abuts with a shoulder 203 of the latch member 202 such that the latch member 202 and the capture member 17 are caused to move in said direction away from the surgical site such that the straightening member 101 is fully removed from the electrode array 100.

The device 10 includes a safety clip 210 which is depicted in FIG. 21, and when used with the device 10 in FIGS. 22a, b and c. The safety clip 210 prevents premature movement of the electrode array positioning member 14 and thus movement of the electrode array 100.

The safety clip 210 is clipped onto a region of the electrode array positioning member 14 adjacent its first end 15. In the embodiment depicted, a region of the electrode array positioning member 14 adjacent said first end 15 extends beyond the proximal end 12 of the housing 11. Movement of the first end 15 of the electrode array positioning member towards the proximal end 12 of the housing allows the electrode array 100 to advance off straightening member 101 and into a cochlea of a subject. The safety clip 210 abuts with the proximal end 12 of the housing 11 thereby preventing any such forward movement of the electrode array positioning member 14.

Further Embodiments

In a first aspect, the present invention consists in a device for implanting an electrode array into the body of a subject and removing a straightening member of the electrode array, the device including a main body which extends from a proximal end to a distal end wherein the distal end receives at least a portion of the electrode array, the device further including an electrode array positioning member that is movable from a first position to a second position, said movement of the electrode array positioning member from its first position to its second position effecting movement of the electrode array from a first position wherein it is housed relatively within the main body to a second position wherein a substantial length of the electrode array extends from the distal end of the main body; the device further including a capture member which engages at least a portion of the straightening member of the electrode array and restricts said straightening member moving with the electrode array to its second position upon movement of the electrode array positioning member.

In a preferred embodiment, the electrode array is implanted in a cochlea of a subject.

In a second aspect, the present invention provides a system for inserting an electrode array into a cochlea of a subject, said system comprising:

a pre-curved electrode array maintained in a substantially straight configuration by a straightening member positioned along a substantial length of said array; and an insertion device for receiving said electrode array;

wherein the electrode array is advanced into the cochlea of a subject by the insertion device and further wherein the straightening member of the electrode array is substantially prevented from advancing into the cochlea by said insertion device such that as the electrode array is advanced into the cochlea said electrode array can gradually assume its pre-curved configuration thereby adopting an advancement path that conforms with the natural shape of the cochlea.

In a third aspect, the present invention provides a system for inserting an electrode array into a cochlea of a subject, said system comprising;

a pre-curved electrode array maintained in a substantially straight configuration by a straightening member positioned along a substantial length of said array;

a loading cartridge for receiving said electrode array; and an insertion device for receiving said loading cartridge with said electrode array positioned thereon;

wherein the insertion device causes the electrode array to advance from the loading cartridge and into the cochlea of a subject whilst substantially preventing the straightening member of the electrode array from advancing into the cochlea such that as the electrode array is advanced into the cochlea said electrode array can gradually assume its pre-curved configuration thereby adopting an advancement path that conforms with the natural shape of the cochlea.

Preferably, the main body of the device forms a housing extending from the proximal end to the distal end. The housing may include a handle and a tip member wherein the handle and tip member may be integral with one another or alternatively, the tip may be removably connected to the handle. The housing may also include an inner member positioned at least partially within an outer member.

The electrode array positioning member may comprise a number of structures and may be moved from its first position to its second position by a number of means. In each embodiment discussed below, it may be seen that movement of the electrode array positioning member in a direction towards the distal end of the housing relative to a substantially fixed capture member allows the electrode array which has been loaded onto the device to effectively "advance off" the straightening member.

In a preferred embodiment, said electrode array positioning member comprises an elongate member that substantially extends through said housing from a first end to a second end, said second end adapted to engage part of the electrode array.

With reference to movement of the electrode array positioning member, the electrode array positioning member may be connected to the handle of the housing such that as the handle is moved in a direction towards the distal end of the housing, said electrode array positioning member is also moved in said direction. In use, this embodiment enables a surgeon to manipulate the device of the present invention much like a pen.

Alternatively, the electrode array positioning member may comprise a plunger member. In this embodiment, it is preferred that a length of the electrode array positioning member adjacent the first end of the electrode array positioning member extends beyond the proximal end of the housing. When the device is in use, the surgeon may exert pressure on the plunger member to cause movement from its first position to its second position. The plunger member typically includes an actuator member at its first end wherein said actuator member, which may be a thumb rest, is adapted to abut with the proximal end of the housing. This abutment limits movement of the electrode array positioning member towards the distal end of the housing thus ensuring that a user does not advance an electrode array too far into a cochlea of a subject.

Still further, the electrode array positioning member may be connected to or brought into engagement with a slider such that movement of the slider towards the distal end of the housing causes movement of said electrode array positioning member in said direction. The slider may move along a slot in the wall of the housing and include finger rests to enable a user to move the slider along said slot.

The second end of the electrode array positioning member may be forked, grooved or slotted to optimize engagement with the electrode array.

Alternatively, at least a portion of the electrode array positioning member adjacent the second end may comprise a substantially hollow cylinder defining an internal lumen therein. In this regard, it is preferred that in addition to being adapted to engage and position an electrode array, the lumen of the electrode array positioning member also receives an engagement portion of the straightening member of the electrode array.

Similarly, the electrode array positioning member may include a grooved or recessed portion at or adjacent its second end to receive the engagement portion of the straightening member.

In another embodiment, the housing may include an inner member and an outer member. The inner member and the outer member typically make up part of the tip member of the housing and are configured such that one of said inner member or outer member is fixed relative to the other member such that the relatively "movable" member may include the electrode array positioning member and the substantially "fixed" member may include the capture member.

The capture member may include a number of structures but in each embodiment has the feature that it engages and "captures" the engagement portion of the straightening member such that as the electrode array is advanced into a cochlea of a subject during a procedure, the engagement portion of the straightening member is held by the capture member and the electrode array is allowed to "advance off" the straightening member. In this regard, the capture member may be essentially fixed relative to the electrode array positioning member.

By the term "substantially fixed", it is considered that the capture member does not substantially move in a direction towards the distal end of the housing of the device, which, when the device is in use, is towards a cochlea of a subject. It is envisaged, however, that the capture member may be moved relatively in a direction away from the distal end of the housing such that the straightening member of the electrode array may be fully removed from an electrode array.

In a preferred embodiment, the capture member may comprise an elongate member which extends from one end to a capture end. At or adjacent the capture end said capture member may include a flap, hook, loop or tie or any member capable of engaging with the engagement portion of the straightening member when said electrode array is loaded onto the device of the present invention.

Alternatively, the capture end may include a pair of jaw members which are movable from a first open position to a second closed position such that in the second closed position, the jaw members clamp around the engagement portion of the straightening member.

Rather than an elongate member extending through the main body, the capture member may include a member positioned on or forming part of a wall of the housing. For instance, in the embodiment having a tip member which comprises an inner member and an outer member, the capture member may be positioned on one of said inner or outer members. As discussed above, one of the inner member or the outer member is movable relative to the other that is substantially fixed. The capture member may be positioned on said substantially fixed member. The capture member may include a flap, hook, loop or tie or any member capable of engaging with the engagement portion of the straightening member.

It is also preferred that at least a portion of the electrode array positioning member adjacent its second end includes a slot along its wall. Said slotted portion may receive at least part of the capture member.

In the embodiment wherein the electrode array positioning member is an elongate structure extending from a first end to a second end and the capture member also comprises an elongate structure extending from one end to a capture end, it is envisaged that the capture end of the capture member may comprise a substantially hollow cylinder. The second end or a portion adjacent the second end of the electrode array positioning member is receivable within a lumen formed by the substantially hollow cylinder of the capture member. The flap, hook, loop or tie member of the capture member preferably extends inwardly of the capture end such that it may engage the engagement portion of the straightening member received by the electrode array positioning member.

In the embodiment wherein the capture member is positioned on a wall of an inner member or an outer member of the tip member of the housing, it is preferred that the inner member and the outer member are substantially hollow in structure such that the inner member is slidably receivable within the outer member.

In one embodiment, the electrode array positioning member may comprise the inner member. In this embodiment, the capture member is positioned on the outer member such that at least part of the capture member extends through the slotted portion of the electrode array positioning member.

In another embodiment, the electrode array positioning member may comprise the outer member and the inner member includes the capture member. In this embodiment, the electrode array may be received within both the inner and the outer members such that the engagement portion of the straightening member of the electrode array extends into the lumen of the inner member and engages with the capture member. The outer member engages the electrode array such that as the outer member is moved so too is the electrode array.

The capture member preferably includes a flap member made from a resiliently flexible material such as a plastics material. In this embodiment, the principle of capture of the engagement portion of the straightening member of the electrode array relies upon movement or deformation of the flap member caused by movement of the engagement portion through the lumen of the electrode array positioning member as the electrode array is loaded onto the device of the invention. In this regard, the force of the moving engagement portion of the straightening member against the flap member causes the flap member to move from a first position substantially occluding the lumen of the electrode array positioning member to a second position which allows passage of the engagement portion of the straightening member past the flap member. Upon release of the "deforming" force, i.e. once the engagement portion has passed the flap member, said flap member may return to its original configuration such that it substantially occludes the lumen of the electrode array positioning member and prevents the engagement portion from moving in a reverse direction. This may be achieved in a number of ways as discussed in further detail below.

Alternatively, the capture member may include a hook, press stud, or other like member that extends from the capture member and into the lumen of the electrode array positioning member whereupon it engages a complementary structure such as a loop member comprising the engagement portion of the straightening member.

In the embodiment wherein the capture member includes a pair of jaw members at its capture end, it is envisaged that the jaw members are made from a suitably malleable material to allow movement of said jaw members from a first open position to a second closed position. In one embodiment, the jaw members may be moved to their closed position by movement of the electrode array positioning member. In this regard, the capture member may be positioned within at least the substantially hollow cylinder of the second end of the electrode array positioning member such that the jaw members extend beyond the second end and flare outwardly from said second end. Movement of the electrode array positioning member to its second position causes the second end of the electrode array positioning member to abut with the flared out jaw members. The continued force applied to the jaw members as the electrode array positioning member moves from its first to its second position causes said jaw members to deform and take on their second closed position thereby capturing the engagement portion of the straightening member of an electrode array loaded onto the device.

The straightening member of the electrode array typically extends through a central lumen or along a slot in the electrode array from a proximal end of said electrode array to a leading tip of the electrode array. The straightening member acts to straighten a pre-curved electrode array thus enabling insertion of the electrode array through a cochleostomy and into the cochlea.

Typically, said engagement portion of the straightening member which is captured by the capture member extends beyond the proximal end of the electrode array and may include a number of structures including but not limited to a substantially spherical member, a hemispherical member, a conical member, a bullet-like member, or an arrow-shaped member. Alternatively, as mentioned above, the engagement portion may include a loop or other like structure or a combination of a loop with any one of the substantially spherical, hemispherical, conical, bullet-like, or arrow-shaped members. In this latter embodiment, it is preferred that the loop is located furthest from the electrode array than either the substantially spherical, hemispherical, conical, bulletlike, or arrow-shaped member. This has the advantage that a surgeon may maintain the option of inserting the electrode array manually wherein the loop may be more easily captured by a hand tool such as a hook, forceps, tweezers or the like.

In a further embodiment, the engagement portion of the straightening member may comprise a structure such as a substantially spherical, hemispherical, conical, bullet-like, or arrow-shaped member having an aperture therein such that said aperture may act as a means of manual capture of the straightening member and the substantially spherical, hemispherical, conical, bullet-like, or arrow-shaped member as a means of deforming the flap member and resulting in capture of the engagement portion of the straightening member.

In one embodiment, the electrode array may be loaded into a cartridge member with the engagement portion of the straightening member extending from one end of the cartridge member. The end of the cartridge member with the engagement portion of the straightening member extending therefrom is received within the distal end of the housing of the device. As the cartridge member is loaded onto said distal end, said portion of the straightening device may be caused to move through the lumen of the substantially hollow portion of the electrode array positioning member and along the slotted portion of the electrode array positioning member.

As discussed above, at least part of the capture member may extend into the slot formed in the wall of said slotted portion. Where the capture member includes a flap member, the flap member typically extends into and substantially occludes the lumen of the hollow cylinder of the electrode array positioning member. In the embodiment wherein the flap member is made from a resiliently flexible material, as the engagement portion of the straightening member is moved into and along the slotted portion of the electrode array positioning member, the engagement portion of the straightening member is forced against the flap member causing said flap member to move or deform such that it no longer substantially occludes the lumen of the electrode array positioning member. This allows the engagement portion of the straightening member to pass the flap member. Once the engagement portion of the straightening member has moved beyond the flap member, the flap member may resume its original configuration extending through the slot of the slotted portion of the electrode array positioning member and into the lumen of the electrode array positioning member and substantially occluding said lumen.

Typically, the flap member may only be movable or deformable in one direction to allow the engagement portion of the straightening member to pass. The flap member therefore acts as a "one-way gate" for the engagement portion of the straightening member.

In a preferred embodiment, when the electrode array is loaded onto the device, the second end of the electrode array positioning member abuts with the proximal end of the electrode array. In the embodiment wherein the electrode array positioning member comprises a plunger member, when the plunger member is moved in a direction towards the distal end of the housing, the second end of the electrode array positioning member pushes the proximal end of the electrode array such that the electrode array is advanced from the distal end of the housing, and when used in a surgical procedure, advanced into a cochlea. of a subject.

As the electrode array is advanced into the cochlea, the engagement portion of the straightening member captured by the flap member is held by the "one way gate" system of the flap member and thus prevented from advancing with the electrode array. The entire straightening member is, therefore, prevented from advancing into the cochlea with the electrode array and the electrode array "advances off" the straightening member and into the cochlea. Substantially free of the straightening member, the electrode array may then start to take on a pre-curved configuration within the cochlea of the subject.

To fully remove the straightening member from the electrode array, the capture member may be moved in a direction towards the proximal end of the housing. Where the capture member includes a flap member, such movement causes the flap member to abut with part of the engagement portion of the straightening member and pull the engagement portion of the straightening" member along the slotted portion of the electrode array positioning member in a direction towards the proximal end of the housing.

In this regard, the capture member may be connected to a slide member which may be positioned on an outer wall of the housing or, alternatively, within the housing and having a portion extending from the housing to enable manipulation of said slide member by a user. The capture member may be connected to said slide member by a number of means including by a tie member or, alternatively, by a pulling rod. The slide member typically includes two fingers rests which extend from said slide member and through two opposing slots in the wall of the housing. A user may therefore move the finger rests along the slots of the housing to effect movement of the capture member. Movement of the finger rests in a direction towards the proximal end of the housing typically effects full withdrawal of the straightening member from the electrode array.

The device of the present invention may further comprise a safety mechanism to prevent withdrawal of the straightening member before the electrode array positioning member has moved to its second position and the electrode array advanced into the cochlea of a subject. In this regard, typically, the slide member has a spring member housed in a recess of said slide member. The spring member is preferably made from a resiliently flexible material and includes a main body which, on one side is hingedly connected to a leg member. On an opposing side of the main body, the spring member includes a housing engagement portion which extends from the main body and into a niche in the inner wall of the housing of the device. When the housing engagement portion is positioned within the niche of the housing, any movement of the spring member and the slide member relatively towards or away from the distal end of the housing is prevented.

The slide member and the main body of the spring member may further include a groove which receives a portion of the electrode array positioning member thereby allowing the electrode array positioning member to pass through the groove of the slide member as the electrode array positioning member is moved from its first to its second position.

Typically, the electrode array positioning member comprises a number of components connected to or integral with one another. Preferably, the electrode array positioning member includes a plunger member made up of a thumb rest connected to or integral with a pushing arm. The thumb rest and pushing arm are preferably made from a relatively hard material such as a hard plastics material. The pushing arm may be connected to or integral with an intermediate member which is typically made from a relatively more flexible material than the thumb rest and pushing arm. Further, the intermediate member can have a smaller cross-sectional diameter than the pushing arm. Finally, the intermediate member is connected to or integral with an end member which receives the electrode array. The end member is typically made from a suitably biocompatible material such as surgical stainless steel or titanium.

Preferably, a portion of the pushing arm adjacent its connection with the intermediate member is tapered to form a shoulder.

In use, the intermediate member typically passes along the groove of the slide and spring member when the plunger is actuated and the electrode array is advanced into a cochlea. Movement of the intermediate member along the groove of the spring member does not disrupt the configuration of the resiliently flexible spring member. Accordingly, if the spring member is positioned such that the housing engagement member is within the niche in the housing, movement of the intermediate member of the electrode array positioning member along the groove does not dislodge said housing engagement member and the spring member, slide member and the capture member (which is connected to the slide member) are therefore prevented from moving either in a direction relatively towards or away from the distal end of the housing, that is, each of these components are fixed relative to the housing and the electrode array positioning member. This enables the electrode array positioning member to be moved to its second position without the risk of the straightening member of the electrode array being withdrawn prematurely from said array.

As the electrode array positioning member reaches its second position, the tapered portion of the pushing arm extends into the groove in the spring member. The shoulder of the pushing arm pushes against a wall of the groove of the main body, causing the main body to move about its hinged joint with the leg member from a first position wherein the main body is relatively spaced from the leg member to a second position wherein said main body is relatively less spaced from the leg member. The leg member is substantially prevented from moving relative to the main body as it is relatively securely housed within a complementary structure of the slide member. Movement of the main body of the spring member relative to the leg member disengages the housing engagement member from the niche in the inner wall of the housing. With the housing engagement member disengaged from the inner wall of the housing, the slide member and the capture member are free to be moved by way of the finger rests in a direction towards the proximal end of the housing.

In a preferred embodiment, the distal end of the housing abuts with the cochlea during the entire procedure of insertion of the electrode array and removal of the straightening member from the electrode array. Such a device provides a stable tool for the insertion of the electrode array with less risk of slippage or accidental movement of the device during insertion of said array.

In another embodiment, the device may include a safety mechanism to prevent the distal end of the housing advancing too far into a cochlea of a subject. For example the device may include a cochleostomy stopper at or adjacent the distal, end which abuts with an edge of a cochleostomy.

Other safety mechanisms include means to prevent the electrode array advancing too far into a cochlea of a subject. In this regard, the device may include at least one stopper member which prevents the electrode array positioning member from moving beyond a predetermined position. In one embodiment, the stopper member may include an engagement member which—engages with a latch member when the electrode array positioning member is in its second position. Such engagement with said latch member prevents the electrode array positioning member moving any further beyond the second position. The latch member may be positioned on any part of the device including on a wall of the housing or may form part of the capture member.

In another embodiment wherein the electrode array positioning member is moved by movement of a slider along a slotted length of the housing, the limiting factor in this case may be the length of a slot in the housing along which the slider may travel.

Preferably, when the electrode array is loaded onto the device of the present invention, a portion of the electrode array extends a distance of approximately 7 to 10 mm from the distal end of the housing. In this embodiment, when the distal end of the housing is brought into abutment with a cochleostomy during a procedure, the leading tip of the electrode array is positioned in the middle of the lumen near the back of the basal turn of the scala tympani such that said leading tip of the electrode does not exert pressure on the surrounding tissue.

As the electrode array is moved to its second position by movement of the electrode array positioning member, the electrode array continues to follow a trajectory along the middle of the lumen of the scala tympani thereby avoiding pressure on the lateral wall of the cochlea thus minimising the potential for trauma to the lateral wall and the modiolar wall.

The device of the present invention may further include a means to release an electrode array loaded thereon. In this embodiment, the electrode array may be released by a surgeon should manual insertion be preferred.

In another embodiment, the device of the present invention includes a safety clip member to prevent premature movement of the electrode array positioning member and thus movement of the electrode array. In this regard, it is envisaged that a surgeon would be required to release the safety clip prior to a surgical procedure.

It is envisaged that the safety clip may be positioned in engagement with the electrode array positioning member at or adjacent its first end. The safety clip may further abut with a portion of the housing such that the electrode array positioning member is prevented from moving to its second position.

Preferably, the safety clip is included in the packaging of the device to provide support during shipment and transportation. As a result, once unpacked, the device is in the correct position for an assembled cartridge and electrode array to be attached.

The housing of the device may be made from a plastics material such as polytetrafluoroethylene (PTFE) or polypropylene. Alternatively, the housing may be made from a metal such as surgical steel, or a combination of metal and/or plastic. The choice of material may depend upon whether the device is manufactured as a re-usable or a disposable device.

Typically, the housing is tapered towards the distal end. Further, it is preferred that the housing is angled in structure such as to provide a good line of vision for a surgeon during insertion of the electrode array. In this embodiment, the electrode array positioning member and the capture member may also be angled along their length to correspond with the angled structure of the housing. Preferably, the angle of the housing is in the region of 20 to 30°.

Typically, the housing includes a handle and a tip member wherein the tip member is angled relative to the handle. As noted above, the tip member may be removably connected to the handle. Further, the tip member may be rotated relative to the handle such that rotational orientation of an electrode array loaded on the device may be set by a surgeon as desired or preferred for each surgery.

Preferably, a region of the housing adjacent the distal end includes a window to allow a user to view the electrode array during loading of the electrode array onto the device.

In a preferred embodiment, if the electrode array is loaded correctly, the user should be able to view the engagement portion of the straightening member of the electrode array which is captured by the capture member through the window.

The electrode array may be mounted on the device during the manufacture of the device. Typically, however, the electrode array is mounted on the device by a surgeon, immediately prior to surgery.

In a fourth aspect, the present invention consists in a device for inserting an electrode array into a cochlea of a subject and removing a straightening member of the electrode array, the device including a housing extending from a proximal end to a distal end, said distal end adapted to receive a portion of the electrode array, the device further including an electrode array positioning member which is adapted to substantially extend through said housing from a first end to a second end, said second end adapted to engage part of the electrode. array such that movement of the electrode array positioning member from a first position to a second position effects movement of the electrode array from a first position substantially within the housing to a second position substantially extending from the distal end of the housing; the device further including a capture member which extends at least partially through the housing and which has a region adapted to engage a portion of the straightening member of the electrode array and prevent said straightening member from moving with the electrode array from said first position substantially within the housing to said second position substantially extending from the distal end of the housing.

In a fifth aspect, the present invention provides a method of inserting an electrode array into a cochlea of a subject using the device of the first aspect, said method including the steps of:

(a) positioning the device with the electrode array loaded thereon into a surgical site of a subject until the distal end of the housing abuts with a cochleostomy in the wall of the cochlea;

(b) causing the electrode array positioning member to move from its first position to its second position such that the electrode array is caused to move from its first position substantially within the housing to its second position substantially extending from the distal end of the housing such that the electrode array is advanced into the cochlea of a subject; wherein the straightening member of the electrode array is engaged and held by the capture member of the device such that said straightening member does not advance into the cochlea with the electrode array; and (c) withdrawing the device of the invention from the subject.

In a sixth aspect, the present invention consists in a cartridge member for an electrode array, said electrode array having a straightening member, the cartridge member including an elongate body extending from a first end to a second end, said elongate body having an internal lumen extending therethrough which is adapted to receive the electrode array; the cartridge member further including a window in a portion of the sidewall of the elongate body adjacent the first end wherein said window enables a user to view a portion of the electrode array.

The electrode array may be loaded onto the cartridge member of the sixth aspect by feeding a portion of the straightening member of the electrode array which extends from said electrode array into the second end of the cartridge member.

The elongate body further includes a slot along at least a portion of its length to accommodate the leads of the electrode array. Preferably, the slot is substantially straight and constant in width as it extends along said at least a portion of the elongate body.

The electrode array is preferably oriented such that the electrical leads of the electrode array are substantially aligned with said slot of the cartridge member. The electrode array may then be guided into the cartridge member by pulling lightly on the electrical leads of the electrode array until the portion of the straightening member which extends from the electrode array also extends from the first end of the cartridge member.

The cartridge member and electrode array may be used with the device disclosed in the first aspect of the invention wherein the cartridge member may be loaded onto the distal end of the housing of the device and the electrode array positioning member of the device caused to engage the electrode array within the cartridge member. The cartridge may come pre-loaded with the electrode array or, alternatively, a surgeon may load the electrode array onto the cartridge prior to a procedure.

In a preferred embodiment, a portion of the housing adjacent the distal end of the housing of the device includes a window. In this embodiment, as the cartridge member is loaded onto the device of the first aspect, the window of the cartridge member is aligned with the window in the housing of the device.

Typically, if the engagement portion of the straightening member can be seen through the window of the housing, the cartridge member and electrode array may be taken to be correctly mounted and a user may then commence with the surgical procedure.

In a preferred embodiment, the cartridge may be made from a number of materials and is preferably made from an electrically insulating material. Preferably, if not made of such a material, the cartridge includes an electrically insulating layer between the elongate body of the cartridge member and the electrode array. In this embodiment, a metal cartridge member may be coated on an inner wall defining the lumen of the main body with, for example, Paralyne, PTFE, a lubricious silicone, or a plastic paint such as ABS.

In a seventh aspect, the present invention provides an electrode array for insertion into a cochlea of a subject, the electrode array including an elongate body which extends from a proximal end to a distal end and a straightening member extending along at least part of the length of the elongate body wherein at least a portion of the straightening member extends beyond the proximal end of the elongate body, said at least a portion including a substantially spherical member, a substantially hemispherical member or an arrow-shaped member.

In an eighth aspect, the present invention is a method of implanting a pre-curved electrode array into a cochlea of a subject, said pre-curved electrode array being maintained in a substantially straight configuration by a straightening member, said method including the steps of advancing the pre-curved electrode array into the cochlea; and progressively removing the straightening member from the electrode array during insertion such that the electrode array assumes an advancement path that conforms to the natural shape of the cochlea thereby reducing the incidence of damage to the sensitive structures of the cochlea.

It will be appreciated by persons skilled in the art that numerous variations and modifications may be made to the invention as shown in the specific embodiments without departing from the spirit or scope of the invention as broadly described. The present embodiments are, therefore, to be considered in all respects as illustrative and not restrictive.

The invention claimed is:

1. A system for inserting an electrode array into a cochlea of a subject, said system comprising:
   a straightening member configured to physically straighten a pre-curved electrode array;
   the pre-curved electrode array configured to be maintained in a substantially straight configuration when said straightening member is positioned along a substantial length of said electrode array;
   a cartridge configured to receive said electrode array; and
   an insertion device configured to receive at least a portion of said cartridge when said electrode array is positioned therein;
   wherein said insertion device is configured to effect movement of said electrode array from a first position to a second position relative to the insertion device and to substantially prevent said straightening member from moving with said electrode array from said electrode array's first position to said electrode array's second position.

2. The system of claim 1, wherein said cartridge comprises:
   an elongate body having first and second ends and a lumen extending therethrough, wherein said elongate body is configured to receive the electrode array in said lumen.

3. The system of claim 1, wherein said cartridge is formed from an electrically insulating material.

4. The system of claim 2, wherein said cartridge further comprises:
   a slot configured to accommodate an electrical lead extending from the electrode array when the electrode array is inserted into said cartridge.

5. The system of claim 2, wherein said cartridge further comprises:
   a first opening at said first end; and
   a second opening at said second end.

6. The system of claim 1, wherein said cartridge comprises:
   an elongate body extending from a first end to a second end and having a lumen extending therethrough, wherein said elongate body is configured to receive said electrode array in said lumen; and
   an aperture in a sidewall of said elongate body.

7. The system of claim 6, wherein:
   the aperture is a window configured to allow viewing of a portion of said electrode array when said electrode array is positioned in said elongate body.

8. The system of claim 1, wherein said insertion device comprises:
   a housing having a proximal end and a distal end including an aperture, wherein said distal end is configured to receive said at least a portion of said cartridge.

9. The system of claim 8, wherein said cartridge is configured such that an aperture of said cartridge is aligned with said aperture of said housing when said at least a portion of said cartridge is positioned in said housing.

10. The system of claim 9, wherein said system is configured such that a portion of said straightening member is visible through said aperture of said cartridge and said aperture of said housing when said apertures are aligned.

11. The system of claim 9, wherein said insertion device further comprises:
    a capture member having a proximal end disposed within said housing and a distal end configured to engage a portion of said straightening member and to substantially prevent said straightening member from moving with said electrode array from said electrode array's first position to said electrode array's second position.

12. The system of claim 8, wherein said insertion device further comprises:
    an electrode array positioning member configured to substantially extend through said housing, wherein an end of the electrode array positioning member is configured to engage part of said electrode array such that movement of the electrode array positioning member from a first position to a second position relative to the housing effects movement of said electrode array from said electrode array's first position wherein a length of said electrode array is disposed within said cartridge to said electrode array's second position wherein a substantial length of said electrode array extends from said first end of said cartridge.

13. The system of claim 12, wherein a portion of the electrode array positioning member is received in a groove of the insertion device such that the portion of the electrode array positioning member received in the groove moves relative to the groove.

14. The system of claim 1, wherein the cartridge and insertion device form a cartridge-insertion device assembly when the at least a portion of the cartridge is positioned in the insertion device, and wherein the cartridge-insertion device assembly includes a cochleostomy stopper.

15. The system of claim 1, wherein the cartridge and insertion device form a cartridge-insertion device assembly when the at least a portion of the cartridge is positioned in the insertion device, the cartridge-insertion device assembly having an elongated portion extending towards the pre-curved electrode array, and wherein the cartridge-insertion device assembly includes a component extending in a direction generally orthogonal to the direction of extension of the elongated portion and configured to abut tissue of the subject, thereby stopping further travel of the cartridge-insertion device in the direction towards the cochlea.

16. The system of claim 1, wherein:
    at least a portion of the insertion device is made of polytetrafluoroethylene or polypropylene.

17. The system of claim 1, wherein:
    the electrode array includes at least one electrical lead extending therefrom; and
    the cartridge includes a slot extending along a length thereof accommodating the at least one electrical lead of the electrode array.

18. The system of claim 1, wherein:
the cartridge includes a cavity in which the electrode array is received, wherein at least a portion of the cavity is coated.

19. The system of claim 1, wherein:
the cartridge includes at least one inner wall that defines at least a portion of a lumen in which the electrode array is received, wherein at least a portion of the at least one inner wall is coated.

20. The system of claim 1, wherein:
the cartridge includes a groove in a sidewall thereof which receives a portion of the electrode array therein.

* * * * *